(12) United States Patent
Hiroike

(10) Patent No.: US 10,206,642 B2
(45) Date of Patent: Feb. 19, 2019

(54) IMAGING INFORMATION PROCESSING APPARATUS, X-RAY IMAGING APPARATUS, X-RAY IMAGING SYSTEM, CONTROL METHOD, AND PROGRAM FOR CAUSING COMPUTER TO EXECUTE CONTROL METHOD

(71) Applicant: CANON KABUSHIKI KAISHA, Tokyo (JP)

(72) Inventor: Taro Hiroike, Yamato (JP)

(73) Assignee: Canon Kabushiki Kaisha, Tokyo (JP)

( * ) Notice: Subject to any disclaimer, the term of this patent is extended or adjusted under 35 U.S.C. 154(b) by 443 days.

(21) Appl. No.: 14/900,994

(22) PCT Filed: Jun. 27, 2014

(86) PCT No.: PCT/JP2014/067170
§ 371 (c)(1),
(2) Date: Dec. 22, 2015

(87) PCT Pub. No.: WO2014/208722
PCT Pub. Date: Dec. 31, 2014

(65) Prior Publication Data
US 2016/0143602 A1  May 26, 2016

(30) Foreign Application Priority Data

Jun. 28, 2013 (JP) .................................. 2013-137047
Oct. 30, 2013 (JP) .................................. 2013-226013

(51) Int. Cl.
*H05G 1/64* (2006.01)
*A61B 6/00* (2006.01)

(52) U.S. Cl.
CPC .............. *A61B 6/463* (2013.01); *A61B 6/465* (2013.01); *A61B 6/5258* (2013.01); *A61B 6/54* (2013.01);
(Continued)

(58) Field of Classification Search
CPC ..... A61B 6/4233; A61B 6/032; A61B 6/5258; A61B 6/54; A61B 6/585; A61B 6/42;
(Continued)

(56) References Cited

U.S. PATENT DOCUMENTS 7,119,841 B1 * 10/2006 Sako ........................ A61B 6/00
348/333.05
2008/0049889 A1 * 2/2008 Tsukagoshi ............ A61B 6/032
378/4
(Continued)

FOREIGN PATENT DOCUMENTS

JP  11-128211 A  5/1999
JP  11-155847 A  6/1999
(Continued)

OTHER PUBLICATIONS

International Search Report and Written Opinion for PCT/JP2014/067170 and notification of transmittal of the ISR/WO, dated Jul. 10, 2014 (English translation of International Search Report included herewith).
(Continued)

*Primary Examiner* — Irakli Kiknadze
(74) *Attorney, Agent, or Firm* — Canon USA, Inc. I.P. Division

(57) ABSTRACT

An imaging information processing apparatus including a communication circuit configured to communicate with an X-ray imaging apparatus including an X-ray sensor configured to obtain an X-ray image and an X-ray irradiation detection unit configured to detect irradiation of X-rays on the basis of an output of the X-ray sensor, causes, in response to receipt of a signal indicating a state of the X-ray sensor, a display unit to display a first indication for permitting irradiation of X-rays and causes, upon receipt of image data obtained in response to detection by the X-ray irradiation detection unit before receipt of the signal, the
(Continued)

display unit to display a second indication corresponding to the image data.

32 Claims, 19 Drawing Sheets

(52) U.S. Cl.
CPC .................. *A61B 6/42* (2013.01); *A61B 6/467* (2013.01); *A61B 6/563* (2013.01)

(58) Field of Classification Search
CPC ......... A61B 6/463; A61B 6/465; A61B 6/467; A61B 6/563; A61B 6/5241; A61B 6/025; A61B 6/06; A61B 6/461; A61B 6/466; A61B 6/468; A61B 6/469; A61B 6/50; A61B 6/5205; A61B 6/5223; A61B 6/4405; A61B 6/4283; A61B 6/542; A61B 6/547; A61B 6/4494; A61B 6/545; A61B 6/56; A61B 6/4266; A61B 6/00; A61B 6/4411; A61B 6/464; A61B 6/037; A61B 6/4241; A61B 6/5235; A61B 6/482; A61B 6/487; A61B 2503/40; A61B 5/0044; A61B 5/055; A61B 6/4085; A61B 6/4441; A61B 6/481; A61B 6/504; A61B 6/5211; A61B 2503/06; A61B 5/0004; A61B 5/0022; A61B 5/1451; H04N 5/32; H04N 5/3597; H04N 5/374; C07D 471/04; G01T 1/24; G01T 1/2928; G01T 7/005
USPC .......................................... 378/19, 98.5, 98.8
See application file for complete search history.

(56) References Cited

U.S. PATENT DOCUMENTS

| | | | | |
|---|---|---|---|---|
| 2008/0237507 A1* | 10/2008 | Enomoto | ............... | A61B 6/583 250/582 |
| 2009/0016491 A1* | 1/2009 | Li | ........................ | A61B 6/032 378/98.5 |
| 2011/0110496 A1* | 5/2011 | Foos | .................... | A61B 6/4405 378/98.5 |
| 2011/0255654 A1* | 10/2011 | Kim | ....................... | A61B 6/482 378/5 |
| 2012/0195407 A1* | 8/2012 | Nenoki | ............... | A61B 6/4283 378/98.5 |

FOREIGN PATENT DOCUMENTS

| | | |
|---|---|---|
| JP | 2008-264528 A | 11/2008 |
| JP | 2011-067334 A | 4/2011 |
| JP | 4684747 B2 | 5/2011 |
| JP | 2012-011036 A | 1/2012 |
| JP | 2012-083307 A | 4/2012 |
| JP | 2012-135697 A | 7/2012 |
| JP | 2012-165312 A | 8/2012 |
| JP | 2012-187195 A | 10/2012 |
| JP | 2012-250023 A | 12/2012 |
| JP | 2013-039197 A | 2/2013 |
| JP | 2013-51657 A | 3/2013 |

OTHER PUBLICATIONS

International Preliminary Report on Patentability Chapter I (Form PCT/ISA/373) for PCT/JP2014/067170, dated Dec. 29, 2015, and Written Opinion for PCT/JP2014/067170, dated Oct. 7, 2014 (English translation of Written Opinion form PCT/ISA/237 included herewith).

\* cited by examiner

| Examination ID | Patient ID | Patient Name | Sex | Date of Birth | Age |
|---|---|---|---|---|---|
| O001 | P333 | Saburo Yamada | Male | 1981/11/11 | 29 |
| O002 | P222 | Jiro Yamada | Male | 2002/2/2 | 7 |
| O003 | P111 | Taro Yamada | Male | 2001/1/10 | 8 |
| O004 | P777 | Hanako Yamada | Female | 1977/7/7 | 12 |
| O005 | P123 | Ichiro Yamada | Male | 2003/3/3 | 3 |
| O006 | P444 | Shiro Yamada | Male | 1964/4/4 | 45 |
| O007 | P555 | Goro Yamada | Male | 1955/5/5 | 54 |
| O008 | P666 | Rokuro Yamada | Male | 1976/6/6 | 33 |

Patient Name:
Date of Birth: / / Age:
Patient ID: Sex: ○Male ○Female ○Other

OK

Patient Name:
Patient ID:
Date of Birth:
Age:
Sex:

Examination ID:

Start Urgent Imaging    Start Examination (b)

Imaging Procedure List

- Esophogram — Sensor A
- Cine Speech — Sensor A
- Tomosynthesis Chest — Sensor A
- Abdomen AP — Sensor A
- Gallbradder — Sensor A
- Tomosynthesis Abdomen — Sensor A
- Chest AP — Sensor A
- Cystogram — Sensor B
- Esophogram — Sensor C
- Barium Enema — Sensor C
- DHT Placement — Sensor B
- Small Bowel — Sensor B
- Upper GI with Air — Sensor C
- Voiding Cystogram — Sensor A
- IVP — Sensor C
- Defography — Sensor C
- BE Gatrographic — Sensor A Patient Name: Taro Yamada
Patient ID: P111
Date of Birth: 2001/1/10
Age: 8
Sex: Male Examination ID: O003

Abdomen AP — Sensor A
Chest AP — Sensor A

Start Urgent Imaging    Start Examination

Sensor A Ready
Sensor B Not Ready Urgent Use: OK
Sensor C Not Ready Urgent Use: NG FIG. 6
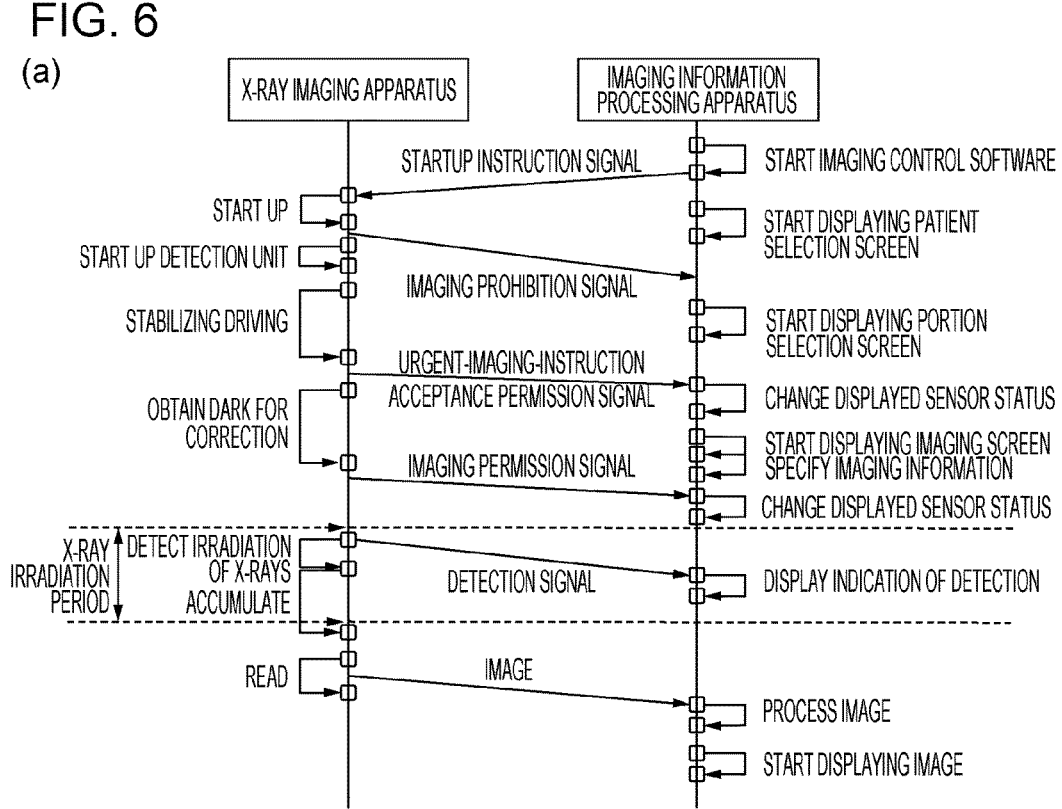
(a)
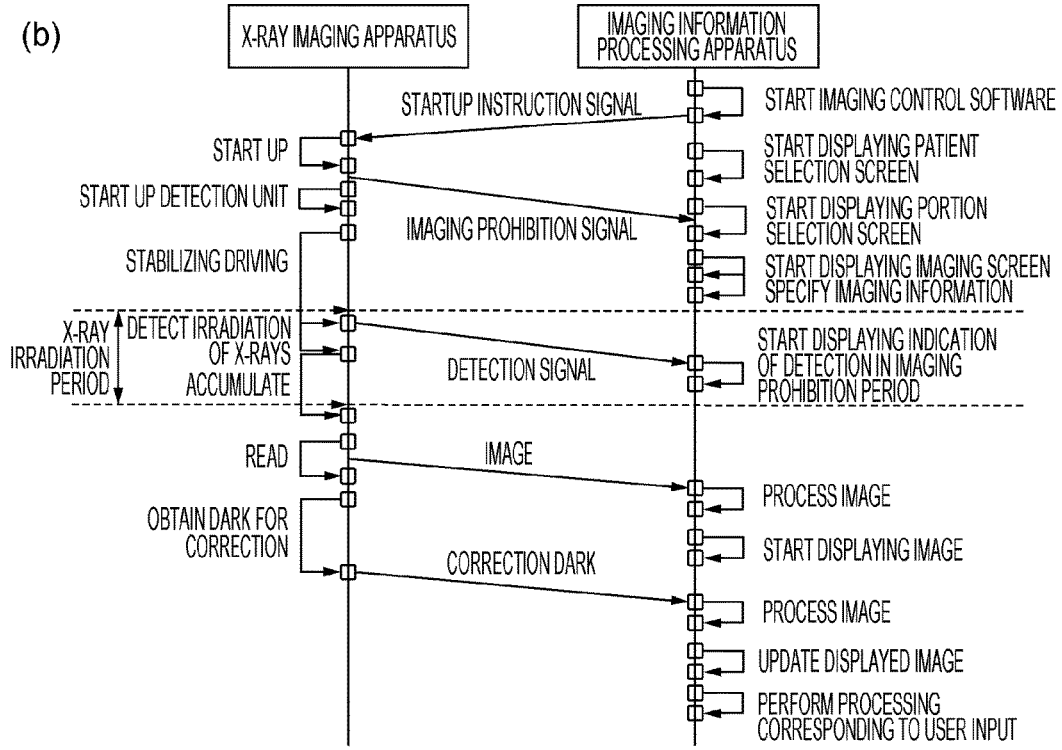
(b)

FIG. 9
(a)
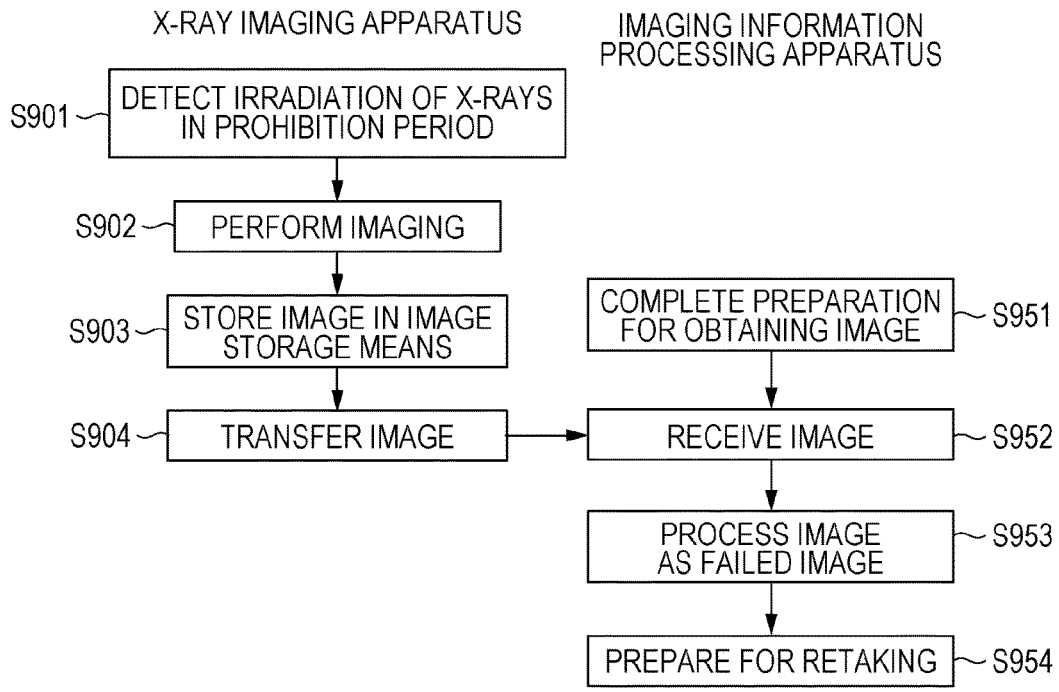
(b)
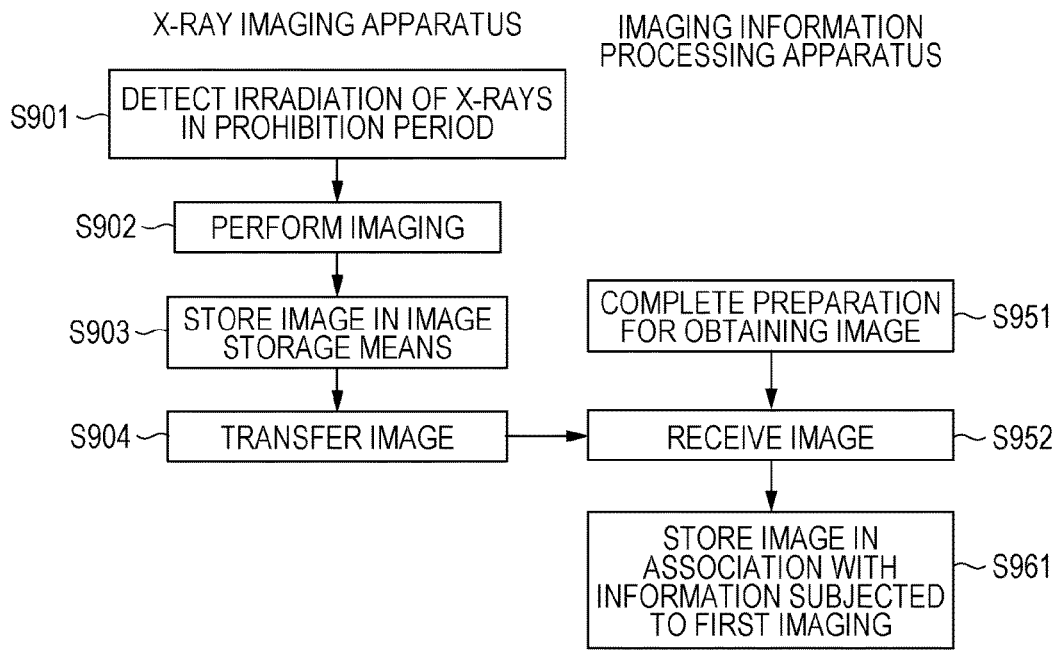

FIG. 10
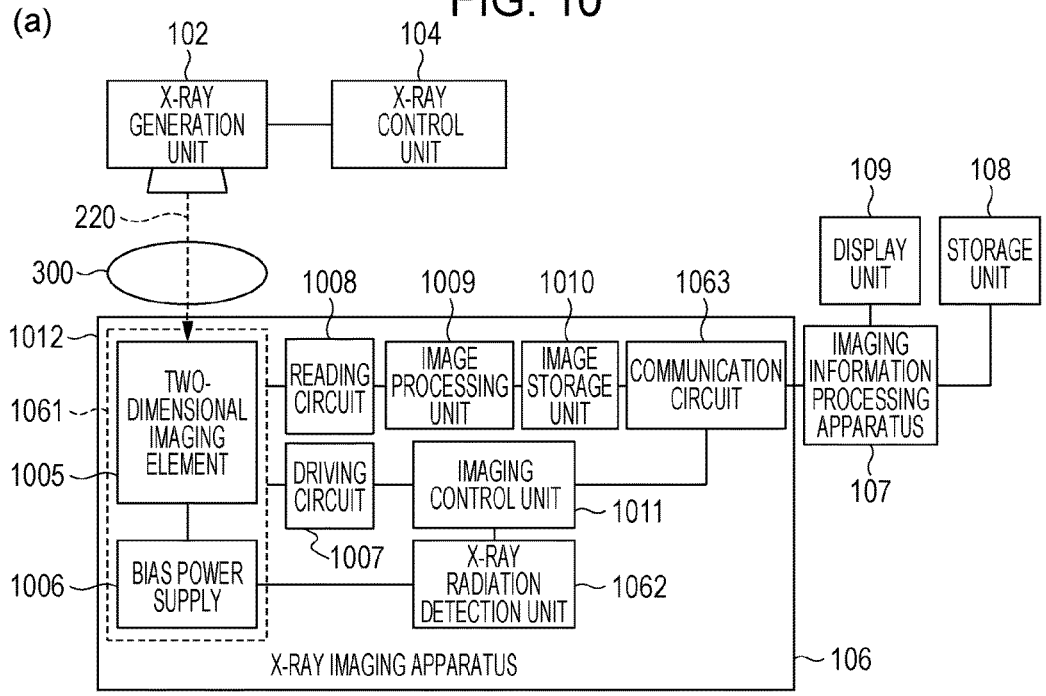
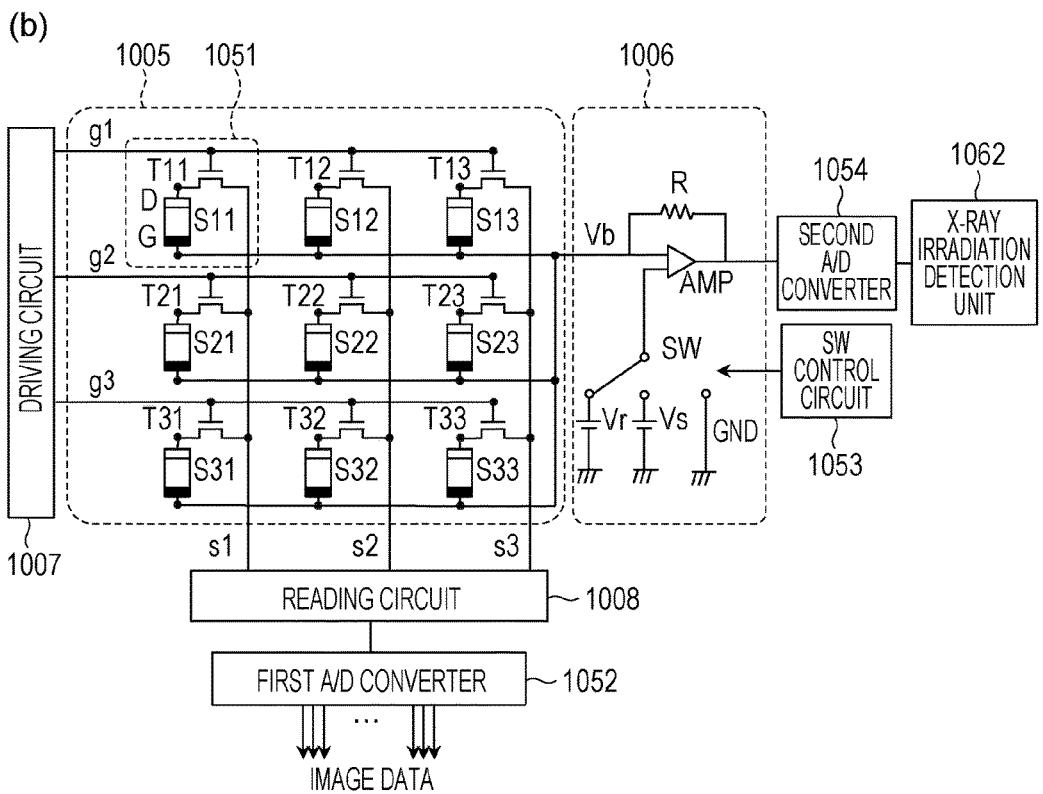

FIG. 15
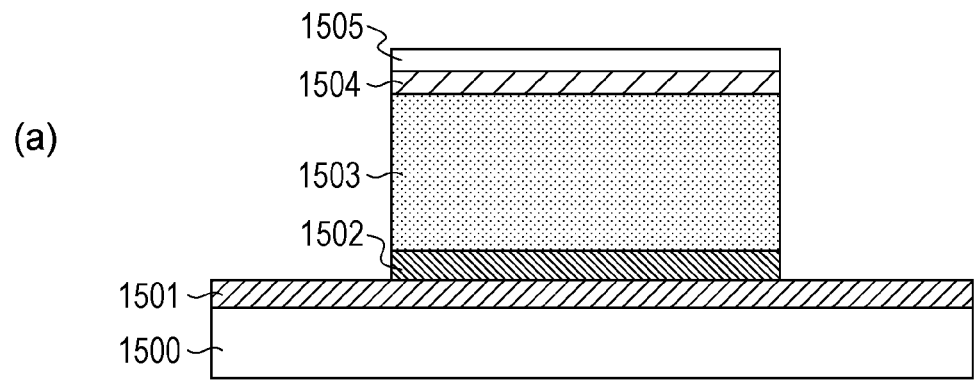
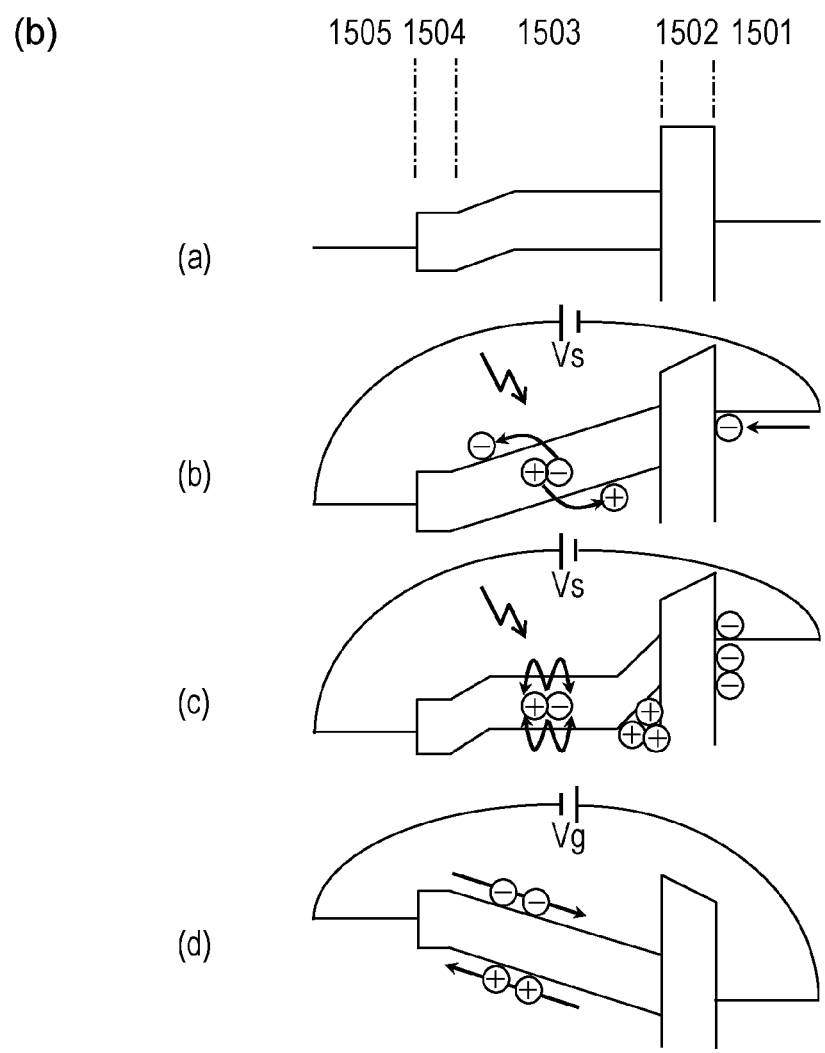

IMAGING INFORMATION PROCESSING APPARATUS, X-RAY IMAGING APPARATUS, X-RAY IMAGING SYSTEM, CONTROL METHOD, AND PROGRAM FOR CAUSING COMPUTER TO EXECUTE CONTROL METHOD

TECHNICAL FIELD

The disclosure in this description relates to an imaging information processing apparatus, an X-ray imaging apparatus, an X-ray imaging system, a control method, and a program for causing a computer to execute the control method.

BACKGROUND ART

X-ray imaging apparatuses that convert radiated X-rays into an electric signal (an amount of electric charges) corresponding to the irradiation dose by using an imaging element have been put to practical use. The imaging element includes small X-ray detectors arranged in a two-dimensional matrix. Each of the X-ray detectors includes a stack of a solid-state photodetector element and a scintillator for converting X-rays into visible light. In such X-ray imaging apparatuses, electric charges generated by irradiation with X-rays can be accumulated in a solid-state photoelectric convertor element typically by controlling the voltage applied to the element. Thereafter, the electric charges are read from the element by setting the voltage to be another voltage, and image data based on the accumulated amount of electric charges is generated.

PTL 1 discloses a system that controls an X-ray radiation timing in accordance with an operation state of an X-ray imaging apparatus by allowing an X-ray generation apparatus and the X-ray imaging apparatus to mutually exchange synchronization signals. PTL 2 discloses a technique for detecting an X-ray irradiation timing by detecting a change in current that occurs in an X-ray imaging apparatus when the X-ray imaging apparatus is irradiated with X-rays and for starting imaging in response to the detection.

CITATION LIST

Patent Literature

PTL 1: Japanese Patent No. 4684747
PTL 2: Japanese Patent Laid-Open No. 11-155847

SUMMARY OF INVENTION

Technical Problem

In the case where a signal for controlling the radiation timing is not sent from the X-ray imaging apparatus to the X-ray generation apparatus, X-rays can be radiated at a given timing with a radiation switch of the X-ray generation apparatus. Accordingly, situations may occur where X-rays are radiated before the X-ray imaging apparatus becomes ready to perform imaging or enters a state where a sufficient image quality is ensured.

Solution to Problem

Accordingly, an information processing apparatus according to an embodiment of the present invention includes a communication circuit configured to communicate with an X-ray imaging apparatus that includes an X-ray sensor configured to obtain an X-ray image and a detection unit configured to detect irradiation of X-rays on the basis of an output of the X-ray sensor, and display control means configured to cause, in response to receipt of a signal indicating a state of the X-ray sensor, a display unit to display a first indication indicating that irradiation of X-rays is permitted and cause, when image data is obtained in response to the detection unit detecting X-rays before receipt of the signal, the display unit to display a second indication corresponding to a fact that the image data is obtained.

Advantageous Effects of Invention

With this configuration, an operator is informed that an image has been obtained as a result of detection of irradiation of X-rays at an inappropriate timing, and thus allowing the operator to appropriately take a subsequent action.

BRIEF DESCRIPTION OF DRAWINGS

FIG. 3(a) is a diagram illustrating an example of a patient selection screen displayed on a display unit by the imaging information processing apparatus. FIG. 3(b) is a diagram illustrating an example of a screen on which imaging information is selected.

FIG. 6(a) is a sequence chart illustrating an example of communication and processing that are performed when irradiation of X-rays is detected in an imaging permitted period. FIG. 6(b) is a sequence chart illustrating an example of communication and processing that are performed when irradiation of X-rays is detected in the imaging prohibited period.

FIG. 9(a) is a flowchart illustrating a flow of a process performed by the X-ray imaging system according to the embodiment. FIG. 9(b) is a flowchart illustrating a flow of a process performed by the X-ray imaging system according to another embodiment.

FIG. 10(a) is a configuration diagram of an X-ray imaging apparatus according to the embodiment. FIG. 10(b) is an equivalent circuit diagram of an X-ray sensor according to the embodiment.

FIG. 15(a) is a schematic diagram illustrating a cross-sectional structure of a photoelectric converter element of the X-ray sensor according to the embodiment. FIG. 15(b) is an energy band diagram in respective operation modes of the photoelectric converter element.

DESCRIPTION OF EMBODIMENTS

Embodiments of the present invention will be described below with reference to the drawings.

Figure 1:
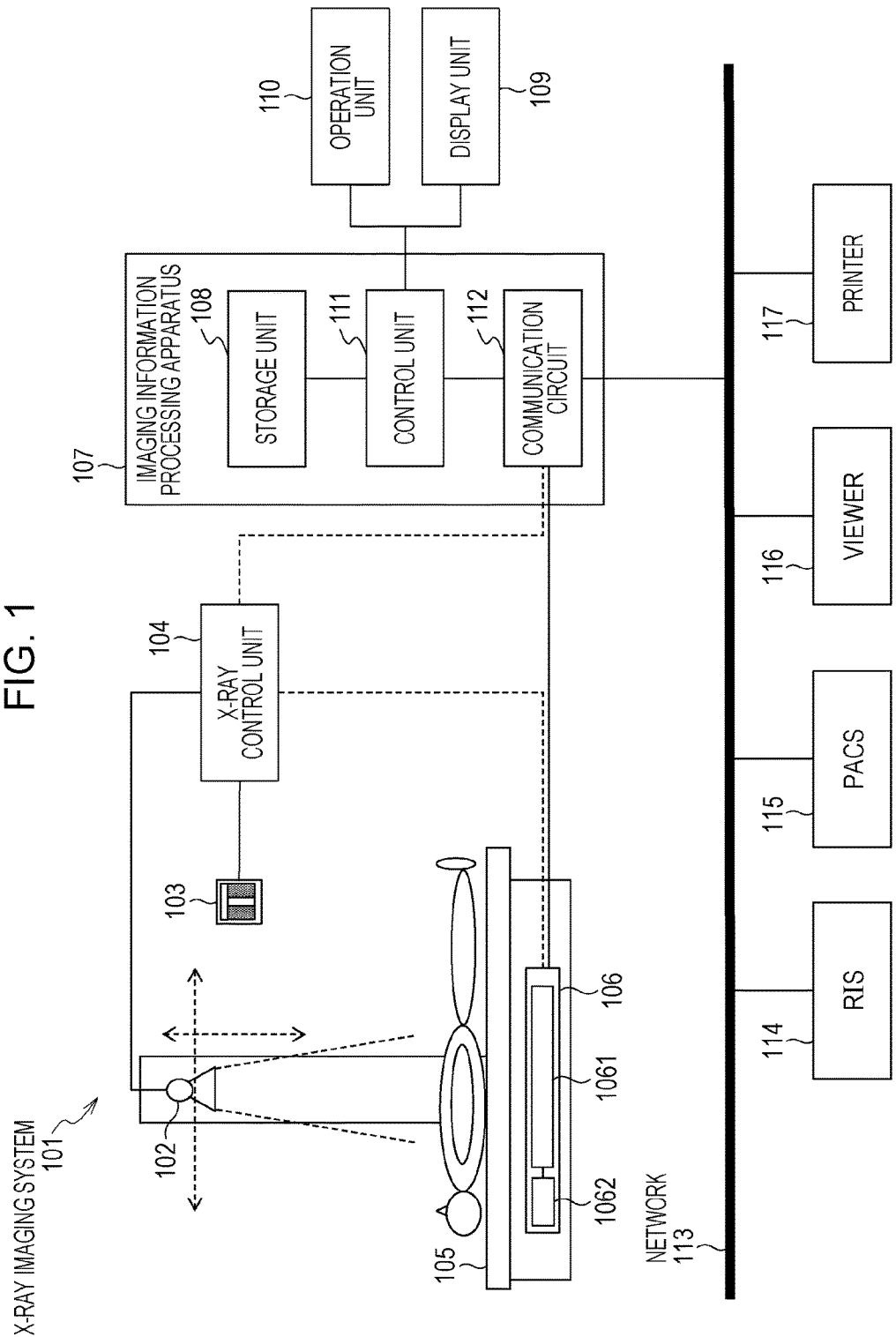
FIG. 1 is a configuration diagram of an X-ray imaging system according to an embodiment of the present invention.

Referring to FIG. 1, a configuration of an X-ray imaging system according to an embodiment of the present invention will be described. An X-ray imaging system 101 according to the embodiment includes an X-ray generation apparatus, a table 105, an X-ray imaging apparatus 106, an imaging information processing apparatus 107, an operation unit 110, and a display unit 109.

The X-ray generation apparatus includes an X-ray generation unit 102, an X-ray radiation switch 103, and an X-ray control unit 104. The X-ray generation unit 102 includes, for example, a target of a reflection or transmission type. The X-ray generation unit 102 causes an electron beam to collide with the target, thereby generating X-rays. A beam of the generated X-rays is shaped by a collimator in the X-ray generation unit and is radiated toward a subject and the X-ray imaging apparatus 106.

The table 105 includes, for example, a table top on which the subject lies, a column that movably holds the X-ray generation unit 102, and a container that movably contains the X-ray imaging apparatus 106. Positions of the X-ray generation unit 102 and the X-ray imaging apparatus 106 are aligned by the table 105, whereby a positional relationship with the subject lying on the table top can be adjusted.

The X-ray imaging apparatus 106 includes an X-ray sensor 1061 that detects X-rays and obtains an X-ray image, and an X-ray irradiation detection unit 1062 that detects irradiation of the X-ray imaging apparatus 106 or the subject with X-rays. The X-ray sensor 1061 includes, for example, a scintillator that converts X-rays into visible light, and an area sensor that converts the visible light into an electric signal. The X-ray irradiation detection unit 1062 detects irradiation of X-rays by continuously and repeatedly monitoring the output of the X-ray sensor 1061, for example. This X-ray irradiation detection unit 1062 is capable of detecting a timing at which X-rays are generated by the X-ray generation unit 102, and consequently a connection between the X-ray generation apparatus and the imaging information processing apparatus 107 is no longer needed. Obviously, communication may be established between the X-ray control unit 104 and the X-ray imaging apparatus 106, and the X-ray control unit 104 and the X-ray imaging apparatus 106 may perform communications for synchronization so that X-rays are generated while the X-ray sensor 1061 is in an accumulation state.

The imaging information processing apparatus 107 includes a control unit 111, a communication circuit 112, and a storage unit 108. The imaging information processing apparatus 107 communicates with the X-ray imaging apparatus 106 via the communication circuit 112. The control unit 111 generates and manages imaging information used to perform X-ray imaging, obtains an X-ray image resulting from the X-ray imaging, and stores the X-ray image in the storage unit 108 in association with the imaging information. The control unit 111 is connected to the operation unit 110 and the display unit 109. The control unit 111 accepts an operation input from the operation unit 110 and sets settings, such as settings for obtaining, generating, and changing the imaging information. The imaging information and the X-ray image are displayed on the display unit 109, thereby permitting the user to check the X-ray image. The operation unit 110 may be a general-purpose operation device, such as a keyboard, a mouse device, or a touch panel; or a dedicated operation device for the imaging information processing apparatus 107.

The imaging information processing apparatus 107 is also connected to a network 113, such as a hospital intranet. The imaging information processing apparatus 107 sends the X-ray image to output destination apparatuses, such as a PACS 115, a viewer 116, and a printer 117, via the communication circuit 112.

An RIS (Radiology Information System) 114 manages a request for radiology information and sends imaging request information to the imaging information processing apparatus 107 of the X-ray imaging system 101. The RIS 114 also manages the progress of the requested imaging. In response to receipt of the imaging request information, the imaging information processing apparatus 107 generates imaging information necessary for imaging and performs X-ray imaging. The imaging information used herein includes a driving condition of the X-ray imaging apparatus 106. In addition to this condition, the imaging information may further include an X-ray radiation condition of the X-ray generation apparatus, an image processing condition for an X-ray image obtained by the X-ray imaging apparatus 106, and an output condition of the processed image, such as cropping. In addition, a given combination of these conditions may be used as the imaging information. When there is a progress in the imaging, such as start or completion, the communication circuit 112 sends progress information to the RIS 114 under control of the control unit 111.

In the case where the imaging information includes the X-ray radiation condition, it is convenient to establish communication to the X-ray control unit 104 and to send the X-ray radiation condition from the communication circuit 112 to the X-ray control unit 104. If there is no communication, an X-ray generation condition is separately input using an operation panel of the X-ray control unit 104.

The PACS (Picture Archiving and Communication Systems) 115 is an image management server. The PACS 115 receives the X-ray image and manages the X-ray image together with other medical images.

The viewer 116 is an apparatus that performs image processing and display control to allow a person who makes a diagnosis, such as a doctor, to view medical images. The viewer 116 may communicate with the PACS 115 to obtain the medical images. The printer 117 outputs the X-ray image and the medical images supplied from the imaging information processing apparatus 107, the PACS 115, and the viewer 116 on a recording medium, such as film or paper.

Figure 2:
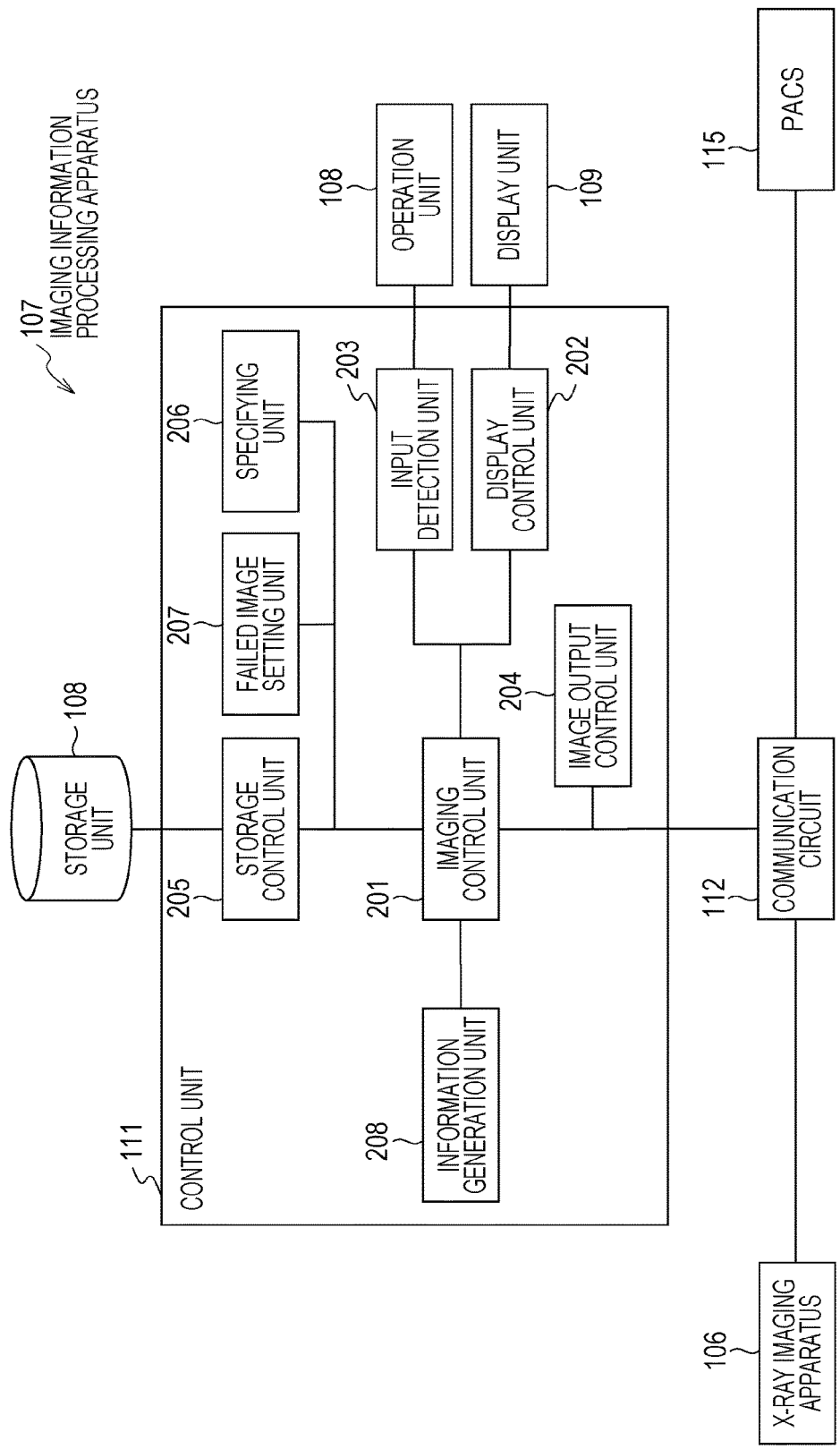
FIG. 2 is a configuration diagram of an imaging information processing apparatus according to the embodiment.

Referring to FIG. 2, a configuration of the imaging information processing apparatus 107 according to the embodiment will be described. The control unit 111 of the imaging information processing apparatus 107 includes an imaging control unit 201, a display control unit 202, an input detection unit 203, an image output control unit 204, a storage control unit 205, a failed image setting unit 207, and a specifying unit 206 that specifies imaging information and an image for which imaging has been done. In addition, the control unit 111 is connected to the storage unit 108, the display unit 109, the operation unit 110, and the communication circuit 112.

The display control unit 202 performs control, such as changing the content of a display screen that is displayed on the display unit 109. The input detection unit 203 detects an operation input from the operation unit 110 operated by an operator, interprets the detected operation input, and obtains instruction information corresponding to the operation input. An image output control unit 204 controls output of an image to the PACS 115. The storage control unit 205 performs control to read data from the storage unit 108 and to store data in the storage unit 108. The imaging control unit 201 integrally controls processing performed by the entire imaging information processing apparatus 107. The imaging control unit 201 performs control, such as instructing each unit of the control unit 111 to start operating/stop operating, inputting an operation parameter, and obtaining output information.

The communication circuit 112 receives, as signals indicating the state of the X-ray sensor 1061, an imaging permission signal (first signal) that indicates a state where irradiation of the X-ray sensor 1061 with X-rays is permitted and an imaging prohibition signal (second signal) that indicates a state where irradiation with X-rays is not permitted. In response to receipt of these signals, the display control unit 202 displays the state of the X-ray sensor 1061 or the X-ray imaging apparatus 106 on the display unit 109. In response to receipt of the imaging permission signal and the imaging prohibition signal, the display control unit 202 displays a symbol or text information that indicates that the X-ray imaging apparatus 106 is ready to capture an X-ray image.

The imaging permission signal or the imaging prohibition signal will be described below. X-ray imaging apparatuses typically accumulate electric charges irrelevant to detection of X-rays even if the X-ray sensor and other peripheral circuits are powered. In addition, even if driving for discharging and outputting these electric charges is performed, an X-ray image of a desired image quality may not be obtained due to issues such as stability of the potential of the X-ray imaging apparatuses. To address such a case, a certain period is provided as a standby period after the discharging output of the electric charges to stabilize the potential. For example, the discharging output of the electric charges and standby are hereinafter referred to as stabilizing driving. In the case where the X-ray generation apparatus and the X-ray imaging apparatus 106 do not perform communication for synchronization, for example, a possibility of X-rays being radiated in a period before the stabilizing driving is started is still left.

In view of the circumstance described above, the X-ray imaging apparatus 106 according to one of embodiments outputs the imaging permission signal in response to the X-ray sensor 1061 entering a state (stabilized state) where an X-ray image of an image quality satisfying a predetermined criterion is obtainable after the startup of the X-ray sensor 1061. The predetermined criterion used herein is determined experimentally. In addition, it is not necessary to determine whether the criterion is satisfied every time by monitoring the output of the X-ray sensor 1061. For example, a period from the start of driving for stabilization (stabilizing driving) may be used as the criterion. Furthermore, this value may be determined at the time of shipment from the factory, and this fixed value may be used as the criterion after the shipment.

For example, after the X-ray imaging apparatus 106 is started up, the X-ray imaging apparatus outputs the imaging permission signal in response to completion of stabilizing driving. Thereafter, in response to imaging, processing such as reading of an image, stabilization of the sensor, and sending of the image is performed. Thus, the X-ray imaging apparatus outputs the imaging prohibition signal. Thereafter, the X-ray imaging apparatus again outputs the imaging permission signal in response to the sensor being stabilized.

The specifying unit 206 specifies, on the basis of instruction information generated by the input detection unit 203 in response to an operation input, an X-ray image or imaging information that is stored in the storage unit 108 or is displayed on the display screen of the display unit 109. In addition, the specifying unit 206 can specify an image or imaging information in response to trigger information fed from the imaging control unit 201, independently from the instruction information from the input detection unit 203.

The failed image setting unit 207 sets, as a failed image, an image that is specified by the specifying unit 206 in response to an operation input from the operation unit 110. A failed image typically indicates an image not suitably used for making a diagnosis, for example. Alternatively, when there are a plurality of images of the same kind, images other than an image most suitably used for making a diagnosis may be specified. Failed image setting information is, for example, information including data that takes a binary value, and a pointer to a target image. The data takes 0 or null for a non-failed image and takes 1 for an image set as a failed image. Such information is set as a failed image by the failed image setting unit 207 or is overwritten in response to the setting of the failed image being canceled. In addition, this information is stored in the storage unit 108 as related information of the target image.

It should be avoided to output images set as failed images from the imaging apparatus to the PACS 115 as images used for making a diagnosis. Accordingly, the image output control unit 208 performs control so that images set as failed images are not output to the PACS 115 even if there is an output instruction. The failed image setting is setting information based on a user operation input, for example. Accordingly, an output setting may be set so that even an image set as a failed image is output to the outside. For example, in the case where an initial setting is set so that a failed image is not output and this setting is changed to output the failed image, even the failed image is output to the outside. In the case where the failed image is output in this manner, information indicating that this image is an image set as a failed image is attached to a DICOM header of the failed image.

The information generation unit 204 generates identification information in accordance with the state that the X-ray sensor is in when the image is received from the communication circuit 112. With this configuration, the imaging information processing apparatus 107 is capable of identifying a period in which the received image is obtained. In terms of this point, the information generation unit 204 and the imaging control unit 201 are an embodiment of a processing unit that allows the imaging information processing apparatus 107 to identify in which period the received image data is obtained.

The identification information is, for example, data indicating whether the image is an image obtained in a period of the state where capturing of an image having an ensured image quality can be performed after the completion of stabilizing driving of the X-ray sensor, for example. Such identification information is attached to a received image by the imaging control unit 201 and is stored in the storage unit 108 together with the image. In this way, the imaging control unit 201 can determine the state of the X-ray sensor when the image is obtained.

Such identification information can take various forms as described later. For example, in the case where irradiation of the X-ray imaging apparatus 106 with X-rays is detected by the X-ray irradiation detection unit 1062 in the period before stabilizing driving of the X-ray sensor completes, the imaging control unit 201 attaches data "0" as additional information. By associating information indicating that the image is obtained in a period before receipt of the X-ray sensor state signal for displaying a first indication indicating permission of irradiation of X-rays on the display unit in this way, the imaging information processing apparatus 107 can inform the user of whether the image possibly involves a problem.

In addition, in the case where irradiation of X-rays is detected by the X-ray irradiation detection unit 1062 in a period after the imaging information processing apparatus 107 receives the X-ray imaging permission signal after stabilizing driving of the X-ray sensor completes, the imaging control unit 201 attaches data "1" as the identification information. Even after the X-ray image is displayed on the display unit 109 by the display control unit 202, if such data becomes null, data 0 is attached in terms of safety in consideration of a possibly of communication with the sensor being not performed appropriately, for example.

As described above, the imaging control unit 201 associates first image data that is obtained in response to detection by the X-ray irradiation detection unit 1062 in a period (first period) for which an indication indicating that irradiation of X-rays is permitted is displayed, with information indicating that the first image data is obtained in the first period. The imaging control unit 201 also associates second image data that is obtained in response to detection by the X-ray irradiation detection unit 1062 in a period (second period) for which the indication is not displayed, with information indicating that the second image data is obtained in the second period. The information associated with this image allows the imaging information processing apparatus 107 to easily inform the user of whether the image possibly involves a problem.

Alternatively, a configuration may be made such that data "1" is attached to an image obtained in response to detection before stabilizing driving and no data is attached to an image obtained in response to detection after stabilizing driving. As described above, a configuration may be made such that information indicating that image data is obtained in the first period is not associated with the second image data that is obtained in response to detection of irradiation of X-rays in a period (second period) for which an indication indicating that irradiation of X-rays is permitted is not displayed.

In addition, the example of the processing unit is not limited to the information generation unit 204 described above. For example, the processing unit may be a determining unit that determines in which period the image is obtained in response to a request of the imaging control unit 201 and that outputs the determination result. Even in this case, information indicating in which period the image is obtained is generated.

In response to the identification process described above, the imaging control unit 201 controls the display control unit 202 in response to receipt of a signal (imaging permission signal) indicating the state of the X-ray sensor 1061 so as to cause the display unit 109 to display the first indication indicating that irradiation of X-rays is permitted. In addition to this, the display control unit 202 causes, in the case of the communication circuit 112 receiving image data that is obtained in response to the X-ray irradiation detection unit 1062 detecting X-rays in a period before the signal is received, the display unit 109 to display the second indication corresponding to the image data. With this configuration, it is possible to inform the operator that X-rays are radiated in an inappropriate period.

In addition, the second indication based on image data may be displayed depending whether or not an indication (first indication) indicating permission of imaging is displayed, instead of defining the cases depending on whether the timing is before receipt of the imaging permission signal.

Various forms of the second indication are conceivable. For example, the display control unit 202 causes the display unit 109 to display, as the second indication, an indication such as changing the color of a message, symbol, window, or specific area indicating receipt of the image data, or making such an indication to blink. In this way, an operator such as a technician is informed that something may be wrong with the image obtained by the X-ray sensor 1061.

In addition, for example, such an image is more likely to have an insufficient image quality than an image obtained by normal imaging. Thus, a failed image button for accepting an operation input instructing whether to set the image data as a failed image is displayed on the display unit 109. If the button is displayed together with, for example, a message informing a possibility of an abnormal image quality, such as "An image possibly having an insufficient image quality is obtained", the operator can more easily grasp the situation. Such an image is more likely to have an insufficient image quality than an image obtained by normal imaging. Thus, a button for accepting an operation input instructing whether to set the image data as a failed image is displayed on the display unit 109. If the button is displayed together with, for example, a message informing a possibility of an abnormal image quality, such as "An image possibly having an insufficient image quality is obtained", the operator can more easily grasp the situation.

In addition, for example, the display control unit 202 displays a retake button for accepting an operation input instructing a retake for the image data, instead of the failed image button described above or together with the failed image button described above. In response to pressing of the retake button, the failed image setting unit 207 sets the received image as a failed image. The imaging control unit 201 additionally generates imaging information corresponding to this imaging. The display control unit 202 displays this additionally generated imaging information together with the imaging information that has already been generated and displayed. With such a configuration, the retake button is displayed in response to obtaining of an image that is highly likely to be a failed image, whereby an operation input for a failed image setting or a retake setting can be omitted.

For example, in response to the button being pressed on the operation unit 110, the failed image setting unit 207 sets the obtained image as a failed image. With such a configuration, an operation performed by the operator can be omitted, and the imaging efficiency can be improved.

In addition, for example, the display control unit 202 displays imaging information specified by the specifying unit 206, and displays image data obtained in response to detection of irradiation before receipt of the imaging permission signal in association with the specified imaging information. As described above, the image can be handled in the same manner as the image data that is obtained in response to detection of irradiation after receipt of the imaging permission signal. For example, in the case where irradiation of X-rays is detected immediately before stabilizing driving ends, it is considered that the X-ray sensor 1061 or the X-ray imaging apparatus 106 is nearly stable. Thus, an X-ray image having an image quality high enough to make a diagnosis may be obtained depending on the circumstance. Accordingly, by handling such an X-ray image in the same way as a normal X-ray image, even an X-ray image that possibly does not satisfy a predetermined image quality criterion can be made usable for making a diagnosis, and an X-ray image that is obtained as a result of the subject being exposed to radiation can be appropriately utilized.

Furthermore, in addition to the example described above, one of the above-described process and a process of displaying the image data in association with the specified imaging information as long as the image data is not specified as a failed image with the above-described button may be selectively executed based on setting information. In this case, the imaging control unit 201 discards the image set as a failed image and adds a radiation dose corresponding to the image to a total radiation dose of the subject. In this case, the image is not displayed. For example, there are cases where the X-ray imaging apparatus 106 detects X-rays in response to irradiation of X-rays irrelevant to diagnosing and obtains an image, such as a case where an X-ray generation operation is checked when there is no subject between the X-ray imaging apparatus 106 and the X-ray generation unit 102. In addition, there are cases where the X-ray irradiation detection unit 1062 erroneously detects irradiation because of a change in current due to a strong impact or vibration depending on the function thereof. An image resulting from such erroneous detection is an image irrelevant to imaging for making a diagnosis. Thus, by performing the process described above, unnecessary data processing can be reduced.

In addition to or instead of the embodiment described above, the display control unit 202 causes the display unit 109 to display a message corresponding to the state that the X-ray sensor is in when the image is obtained. For example, in the case where irradiation is detected after receipt of the imaging permission signal, the display control unit 202 causes the display unit 109 to display an indication indicating that X-rays are detected normally or an indication just indicating that X-rays are detected. In the case where irradiation is detected before receipt of the imaging permission signal, the display control unit 202 causes the display unit 109 to display an indication indicating that irradiation of X-rays is detected in an inappropriate period. Such a configuration makes it possible to present whether irradiation of X-rays is appropriately detected in an easier-to-understand manner for the operator.

Referring to FIG. 3, a patient selection screen and an imaging information selection screen that are displayed on the display unit by the imaging information processing apparatus will be described.

FIG. 3(a) is an example of the patient selection screen displayed by the display control unit 202. The display control unit 202 displays, as a patient selection screen 301, a screen including a patient input area 302, a patient list 303, an OK button 304, a patient display area 305, an imaging information display area 306 for displaying imaging information, an examination start button 307, and an urgent imaging start button 308.

Hereinafter, the expression "button" not only refers to a physical button but also refers to an icon that is displayed on the display unit 109 and that can be specified by an operation input. For example, a pointer icon that moves in response to an input with a mouse or touch panel is placed over the icon, and then the icon is specified, for example, by clicking the mouse or a touch input on the touch panel. Such an operation input is detected by the input detection unit 203. In response to the detection, the imaging control unit 201 starts a function associated with the icon. In addition, specifying the "button" using the pointer icon is also called "pressing".

In the patient input area 302, textboxes and radio buttons used for inputting patient information are displayed. The patient list 303 is a list of patient information candidates extracted from the storage unit 108 in accordance with an input to the patient input area 302. The OK button 304 is a button for confirming selection of a patient who is specified based on the input to the patient input area 302 or from the list 303. The information concerning the selected patient is displayed in the patient display area 305. The examination ID associated with the selected patient is displayed in the imaging information display area 306. Here, an examination is a unit including one or a plurality of imaging sessions, and this unit is determined for each patient. In response to pressing of the examination start button 307, the patient selection screen changes to the imaging information selection screen. In response to pressing of the urgent imaging start button 308, dummy patient information is generated and the patient selection screen changes to the imaging information selection screen without any input to the patient input area 302 or specifying in the patient list 303. Alternatively, in addition to this configuration, for example, the screen may change to the imaging screen after three pieces of dummy imaging information are generated. Such display control is performed under control of the display control unit 202.

The textboxes and the radio buttons of the patient input area 302, patient information in the patient list 303, the OK button 304, the examination start button 307, and the urgent imaging start button 308 are specifiable by an operation input on the operation unit 110. These items are specified under control of the input detection unit 203 and the imaging control unit 201.

FIG. 3(b) illustrates an example of the imaging information selection screen displayed by the display control unit 202. The display control unit 202 displays, as an imaging information selection screen 351, an imaging procedure list 352 including a plurality of imaging information buttons 353, buttons 358 for changing the displayed page of the imaging procedure list 352, a patient display area 354, an imaging information display area 355, selected imaging information 356, an examination start button 357, an urgent imaging start button 359, and state indications 360 that display the states of the X-ray imaging apparatuses.

Each of the imaging information buttons 353 is a button for corresponding imaging information. For example, each of the imaging information buttons 353 displays a portion to be imaged and a corresponding sensor. In response to selection of this button by an operation input on the operation unit 110, the corresponding imaging information is displayed in the imaging information display area 355. For example, in the case where selectable imaging information does not fit within the display area of the imaging procedure list 352, a first button 358a for changing the page of the imaging procedure list 352 to the previous page and a second button 358b for changing the page to the next page are provided as the buttons 358. The displayed imaging information can be changed by selecting such buttons 358. In the patient display area 354, selected patient information is displayed as in the patient display area 305 of the patient input screen 301. In the imaging information display area 355, the examination ID and selected pieces of imaging information 356a and 356b are displayed. In response to pressing of the examination start button 357, the screen changes to the imaging screen for executing the selected imaging information. In response to pressing of the urgent imaging start button 359, one or a plurality of pieces of dummy imaging information are automatically generated without selection of the imaging information buttons 353 in the imaging procedure list 352. Such imaging information is generated by the imaging control unit 201. The imaging control unit 201 selects such dummy examination information, and the display control unit 202 automatically changes the screen to the imaging screen.

State indications 360a, 360b, and 360c are indications for displaying the states of X-ray sensors of a plurality of X-ray imaging apparatuses connected to the imaging information processing apparatus 107.

The state indication 360a displays the state of a sensor A. The state indication 360b displays the state of a sensor B. The state indication 360c displays the state of a sensor C. These state indications are changed in accordance with an imaging permission signal (first signal), an imaging prohibition signal (second signal), or an urgent-imaging acceptance permission signal that is received by the communication circuit 112 from the X-ray imaging apparatus 106. In the example illustrated in FIG. 3(b), the state indication 360a indicates that the sensor A is "Ready", that is, in a state where the imaging permission signal (first signal) has been received and imaging is permitted. The state indication 360b indicates that the sensor B is "Not Ready, Urgent Use: OK", that is, in a state where the first signal has not been received but the urgent-imaging acceptance permission signal has been received, and thus the sensor is stable and imaging can be performed. Urgent imaging will be described in detail in FIG. 6(a). The state indication 360c indicates that the sensor C is "Not Ready, Urgent Use: NG", that is, in a state where the first signal and the urgent-imaging acceptance permission signal (third signal) have not been received, and thus the sensor is unstable and is unable ensure the image quality of urgent imaging. As described above, the state is displayed for each X-ray imaging apparatus in accordance with the state signal from the X-ray imaging apparatus 106, making it easier to grasp which state each X-ray imaging apparatus is in.

Note that the display control described above is performed by the display control unit 202, and the processing of the operation input described above is performed by the input detection unit 203.

Figure 4:
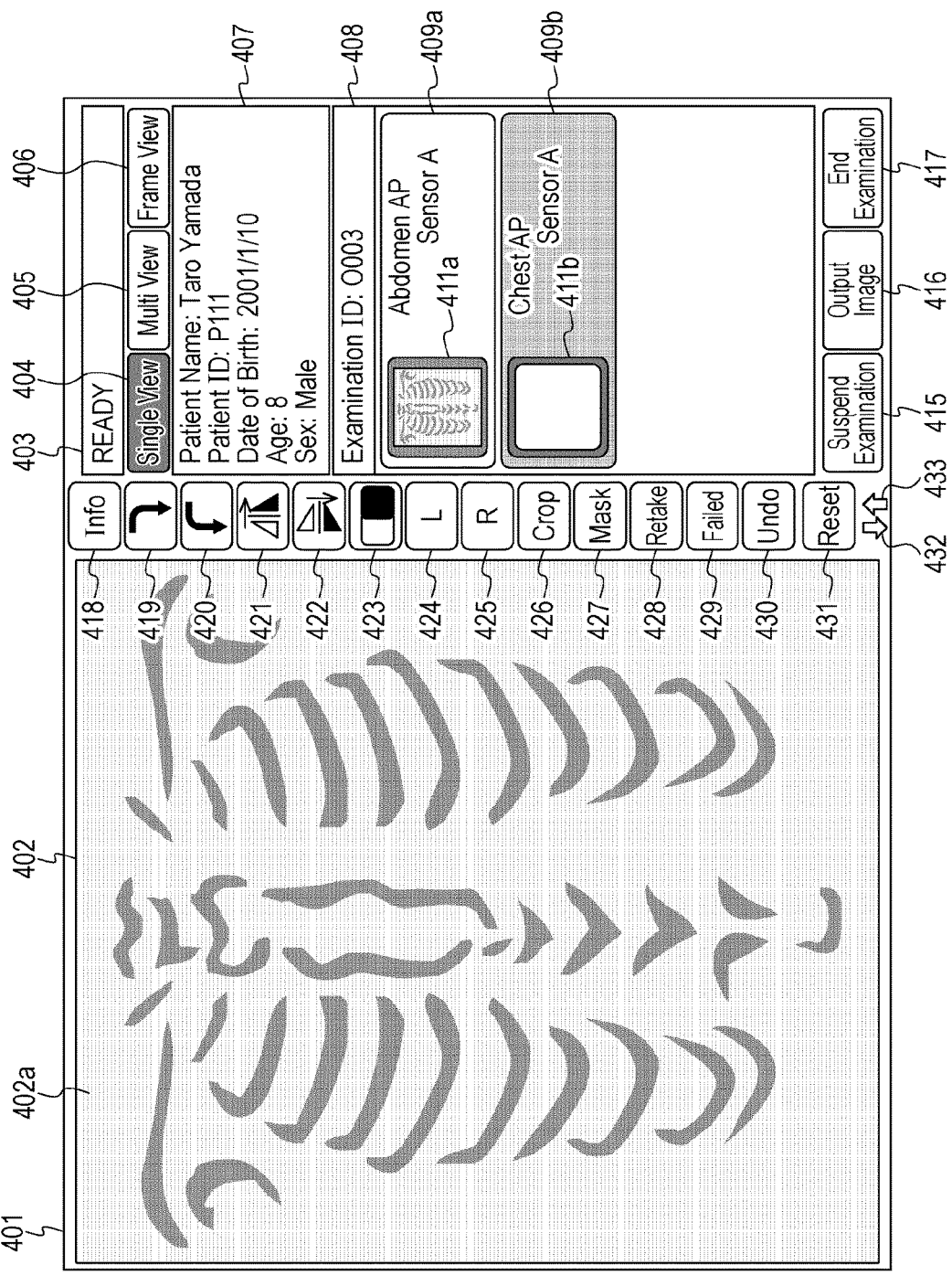
FIG. 4 is a diagram illustrating an example of an imaging screen displayed on the display unit by the imaging information processing apparatus.

Referring to FIG. 4, an imaging screen displayed on the display unit by the imaging information processing apparatus will be described. The display control unit 202 displays, as an imaging screen 401, an image display area 402 for displaying an image 402a, a state indication 403, a patient display area 407, an imaging information display area 408 for displaying imaging information 409, and an examination end button 417. In addition to these, the display control unit 202 may display, in the imaging screen, any one of or any combination of an examination suspend button 415, an image output button 416, a single view button 404, a multi view button 405, a frame view button 406, a details button 418, a −90 degree rotation button 419, a +90 degree rotation button 420, a flip horizontally button 421, a flip vertically button 422, a tone inversion button 423, an L mark button 424, an R mark button 425, a crop button 426, a mask button 427, a retake button 428, a failed image button 429, an undo button 430, a reset button 431, a down button 432, and an up button 433. In the description for FIG. 4 and subsequent figures, display control is performed by the display control unit 202 and processing of an operation input is performed by the input detection unit 203 as in the patient selection screen and the imaging information selection screen described before. Control, such as display control, in accordance with such an input is implemented by the imaging control unit 201. In addition, specifying of an image or imaging information is performed by the specifying unit 206, and a failed image setting is set by the failed image setting unit 207. Details will be described below.

Like the state indications 360, the state indication 403 displays information concerning the X-ray imaging apparatus corresponding to the selected imaging information. In this example, since the X-ray imaging apparatus corresponding to the selected imaging information is the sensor A, the state of the sensor A is displayed. In addition, as illustrated in FIG. 4, the state indication 403 may display the state of the X-ray imaging apparatus (the sensor A in this example) corresponding to imaging information 409b specified as imaging information subjected to the next imaging.

When the single view button 404 is pressed, the display mode is switched to a mode for displaying a specified image alone. FIG. 4 illustrates the state where the image is displayed in the single view mode. The multi view button 405 is a button for switching the display mode to a multi view mode for arranging and displaying captured images in the image display area 402. The frame view button 406 is a button for switching the display mode to a frame view mode for arranging and displaying images of a series of frames of a moving image in the image display area 402. The patient display area 407 is an area for displaying the patient information. The imaging information 409a and the imaging information 409b are a plurality of pieces of imaging information selected for an examination. When imaging is completed, a thumbnail of the resulting image is displayed in a thumbnail display area 411a. No image is displayed in a thumbnail display area 411b of the imaging information 409b for which imaging is not completed. The examination suspend button is a button for temporarily suspending the examination with part of imaging being incomplete as illustrated in FIG. 4. When this button is pressed, the displayed screen changes to the patient selection screen 301 to make another examination selectable. When the image output button 416 is pressed, the image output control unit 208 controls the communication circuit 112 and the storage unit 108 so that images not set as failed images among images obtained by imaging are output to the PACS 115 or the like. When the examination end button 417 is pressed, the examination ends, and the resulting images not set as failed images are output to the PACS 115 or the like.

The details button 418 is a button for accepting an operation input for displaying details of the specified image, imaging information, and patient information. The −90 degree rotation button 419 is a button for rotating the image displayed in the image display area 402 by −90 degrees. The +90 degree rotation button 420 is a button for rotating the image displayed in the image display area 402 by +90 degrees. The flip horizontally button 421 is a button for horizontally flipping the image displayed in the image display area 402. The flip vertically button 422 is a button for vertically flipping the image displayed in the image display area 402. The tone inversion button 423 is a button for displaying an image obtained by inverting the tone of the image displayed in the image display area 402. The L mark button 424 is a button for adding an L mark at a given position in the image displayed in the image display area 402. The R mark button 425 is a button for adding an R mark at a given position in the image displayed in the image display area 402. The crop button 426 is a button for displaying a selection frame for selecting a partial area to be output to the PACS 115 or the like from the image displayed in the image display area 402. The size and position of the selection frame are changeable by an operation input. The mask button 427 is a button for making values of pixels in an area outside the radiation field or the subject to 0 in the image displayed in the image display area 402. The retake button 428 is a button for setting a specified image among images displayed in the imaging information display area 408 as a failed image, generating imaging information including the same imaging condition, the same image processing condition, and the same output condition, and additionally displaying the generated imaging information in the imaging information display area 408. As described above, generation of the imaging information is performed by the imaging control unit 201. The failed image button 429 is a button for setting a specified image among images displayed in the imaging information display area 408 as a failed image. The undo button 430 is a button for canceling the latest processing from among the processing performed by and settings set by the elements 419 to 429 described above. The reset button 431 is a button for cancelling all the processing performed by and settings set by the elements 419 to 429 described above. The down button 432 is a button for displaying buttons that do not fit within the imaging screen 401. When this down button 432 is pressed, the topmost details button 418 is hidden, and another button is displayed. Examples of another button are, for example, buttons such as an enlarge button 434 for enlarging enlarging the image displayed in the image display area 402, a reduce button 435 for reducing the image, a QA button for making detailed image processing settings, and an HQ button for performing image-quality increasing processing. The up button 433 is a button for performing processing opposite to that of the down button 432. When the up button 433 is pressed, the bottommost button is hidden, and a button that is hidden at the top side, for example, the details button 418, is displayed.

X-rays are radiated in response to pressing of the X-ray radiation switch 103 when an indication "Ready" indicating that imaging is permitted is displayed in the state display portion 403 with the imaging information 409b for which imaging is not performed being selected from among the pieces of imaging information displayed in the imaging information display area. The radiated X-rays are detected by the X-ray irradiation detection unit 1062 of the X-ray imaging apparatus 106, and consequently an X-ray image is obtained.

Figure 5:
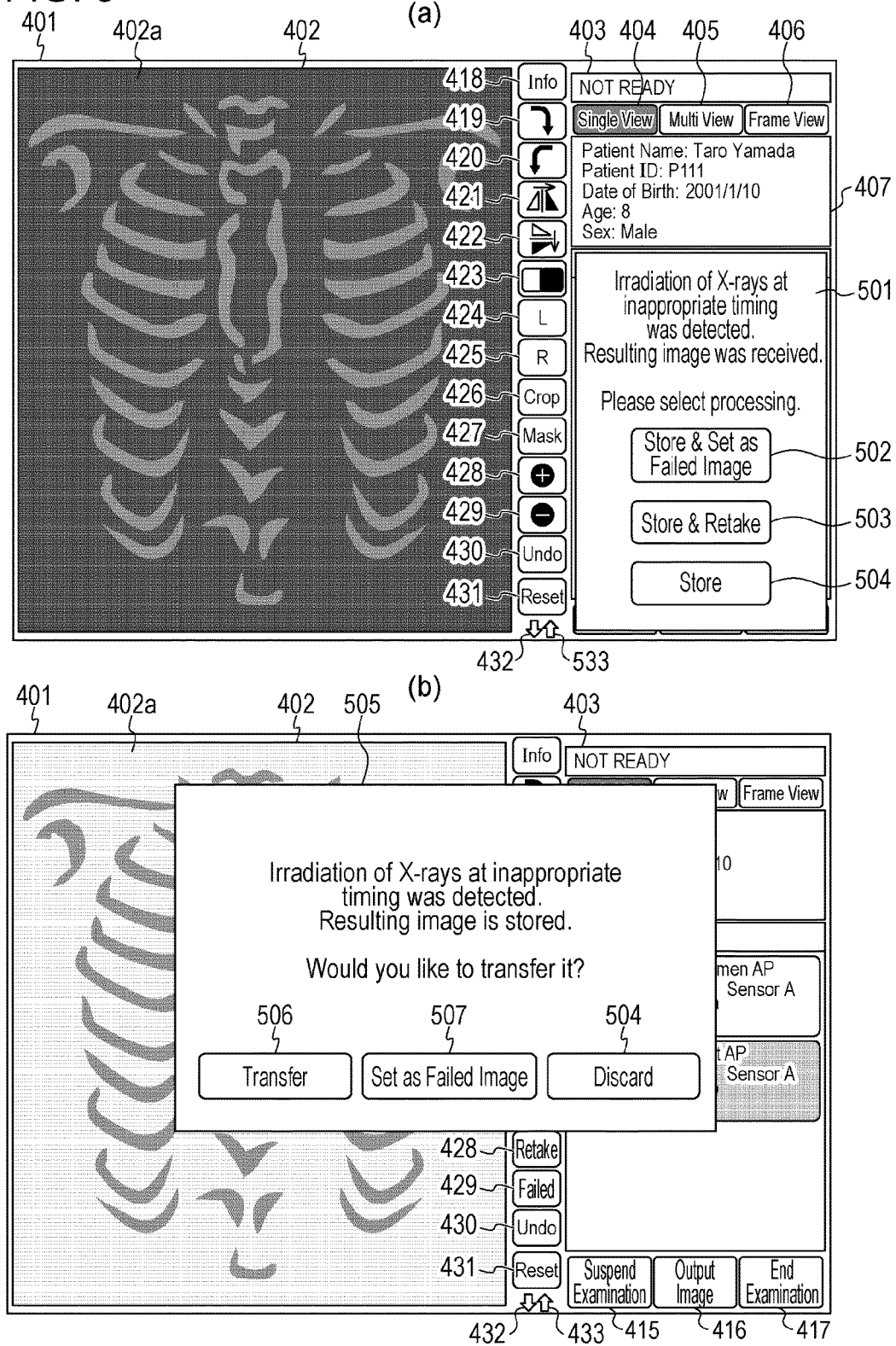
FIG. 5(a) is a diagram illustrating an example of how the imaging screen is displayed when irradiation of X-rays is detected in an imaging prohibited period.
FIG. 5(b) is a diagram illustrating another display example.

Referring to FIG. 5, an example of the imaging screen displayed when irradiation of X-rays is detected in the imaging prohibited period will be described.

A warning indication 501 is displayed on the imaging screen 401 when irradiation of X-rays is detected by the X-ray irradiation detection unit 1062 as a result of the X-ray radiation switch 103 being pressed when "Not Ready", which indicates that imaging is not permitted, is displayed in the state display portion 403. FIG. 5(*a*) illustrates an example of the warning indication. As this warning indication 501, a message, symbol, or figure indicating that X-rays are detected in the imaging prohibited period is displayed. For example, a message such as "Irradiation of X-rays is detected at inappropriate timing" is displayed. Here, for example, in the case where a captured image is received, "The resulting image is received. Please select processing" is displayed as a message indicating that the image is received. The warning indication 501 displays a first button 502 for storing the image and setting the image as a failed image, a second button 503 for storing the image and retaking an image, and a third button 504 for setting the image as a failed image and storing the image without retaking. Like the failed image button 429 and the retake button 428, the first button 502 and the second button 503 execute a process for setting a failed image and a process for retaking, respectively.

As described above, by displaying an indication for an image (second image) obtained at an inappropriate timing together with a message or symbol, it is possible to assist the operator who performs an operation. In particular, an operation for displaying the failed image button 429 or the retake button 428 can be omitted when the failed image button 429 or the retake button 428 is not displayed as in FIG. 5, for example.

In addition, pressing the third button 503 makes it possible to utilize even an X-ray image obtained in an inappropriate period as the diagnosis image if the image quality is sufficiently high for use in diagnosing. With such a configuration, an X-ray image that is obtained as a result of the subject being exposed to radiation can be effectively utilized.

In addition, by displaying the warning indication 501 over the imaging information display area 408, the examination suspend button 415, the image output button 416, and the examination end button 417, the processing can be performed for sure before an operation related to other imaging information or another examination is performed.

In addition, a button for discarding the obtained image may be provided as the warning indication 501.

FIG. 5(*b*) illustrates another example of the warning indication. A warning indication 505 displays a message indicating that an image is stored in the X-ray imaging apparatus 106, such as "Resulting image is stored. Would you like to transfer it?", together with a message, symbol, or figure indicating that X-rays are detected in the imaging prohibited period. Together with these, a transfer button 506 for transferring the image stored in the X-ray imaging apparatus 106, a transfer/failed image button 507 for transferring the image and setting the image as a failed image, and a discard button 508 for discarding the image without transferring it are displayed. In response to pressing of the transfer button 506 and the transfer/failed image button 507, the image is sent from the X-ray imaging apparatus 106 to the imaging information processing apparatus 107. Further, when the transfer/failed image button 507 is pressed, the image is set as a failed image. The discard button 508 is a button for discarding the data in the X-ray imaging apparatus 106 or for sending a signal of an instruction not to transfer from the imaging information processing apparatus 107 to the X-ray imaging apparatus 106 in accordance with an instruction given by the imaging control unit 201.

As described above, by providing a button for performing control so as not to transfer an image that seems to be unnecessary, an unnecessary image transfer is not performed and the efficiency of imaging can be improved.

In addition, the warning indication 505 is displayed, for example, near the center of the imaging screen 401 before the image is transferred to make the other processing not executable unless a button displayed in the warning indication 505 is pressed. In this way, processing can be implemented for sure.

Referring to a sequence chart of FIG. 6, an example of communication and processing performed in the case where irradiation of X-rays is detected in the imaging permitted period will be described.

First, in response to the input detection unit 203 detecting an operation input on the operation unit 110 of the imaging information processing apparatus 107, the imaging control unit 201 starts a imaging control software startup sequence. In response to successful startup of the software, the imaging control unit 102 generates a startup instruction signal for starting up the X-ray imaging apparatus 106 and sends the startup instruction signal from the communication circuit 112 to the X-ray imaging apparatus 106. In response to receipt of the startup instruction signal, the X-ray imaging apparatus 106 starts a startup process. For example, a magic packet in the Wake-on-LAN technology is employed as the startup instruction signal.

After completion of the startup, the control unit of the X-ray imaging apparatus generates an imaging prohibition signal that indicates the state where the X-ray imaging apparatus is not ready to perform imaging and causes the communication circuit to send the imaging prohibition signal to the imaging information processing apparatus 107. In response to completion of the startup, the control unit also supplies power to and start up the X-ray sensor 1061 and the X-ray irradiation detection unit 1062 to enable irradiation of X-rays to be detected.

The control unit then starts stabilizing driving for stabilizing an output of the X-ray sensor 1061. After the stabilizing driving completes, the X-ray imaging apparatus 106 according to one of embodiments sends, to the imaging information processing apparatus 107, an acceptance permission signal for informing the imaging information processing apparatus 107 that an urgent imaging instruction is acceptable.

The control unit then drives the X-ray sensor to perform correction dark obtaining driving. In response to completion of obtaining correction dark, the X-ray imaging apparatus 106 sends an imaging permission signal to the imaging information processing apparatus 107. As a result, preparation to obtain an X-ray image of an appropriate image quality ends.

In response to irradiation of X-rays thereafter, the X-ray irradiation detection unit 1062 detects irradiation of X-rays, and the control unit causes the X-ray sensor 1061 to enter the accumulation state in response to the detection. The control unit also sends, to the imaging information processing apparatus, a detection signal indicating that irradiation of X-rays has been detected. After the accumulation state is maintained for a certain period, the control unit drives the X-ray sensor 1061 to perform reading driving for reading the accumulated electric signal. In parallel to reading, the corresponding image is sent from the X-ray imaging apparatus 106 to the imaging information processing apparatus 107. For example, in the case where a reading circuit is disposed along one side of a pixel array of the X-ray sensor, in response to image data for one line along the side being read by the reading circuit, the communication circuit of the X-ray imaging apparatus 106 sends the image data for the line. Note that transmission of the image may be started after reading of the image data is finished. In addition, the X-ray imaging apparatus 106 may perform dark current correction on the read image data by using the correction dark and transfer the corrected image. Further, other types of correction such as gain correction and defective pixel correction may be performed by the X-ray imaging apparatus 106.

The X-ray imaging apparatus 106 may send the imaging prohibition signal to the imaging information processing apparatus before or after accumulation by the X-ray sensor 1061 is started in response to the X-ray irradiation detection unit 1062 detecting irradiation of X-rays. This imaging prohibition signal may be sent immediately before the detection signal is sent or together with the detection signal.

After the electric signal is read from the X-ray sensor 1061, the control unit of the X-ray imaging apparatus starts stabilizing driving of the X-ray sensor 1061 again and causes the imaging permission signal to be sent after stabilization. The following process is performed similarly.

On the other hand, in the imaging information processing apparatus 107, after the imaging control software is started up, the display control unit 202 causes the display unit 109 to display, for example, the patient selection screen 301 illustrated in FIG. 3(a). A patient is selected in response to an operation input on the operation unit 110 with the screen being displayed. In response to the examination start button 307 being pressed, the display control unit 202 causes, for example, the portion selection screen or the imaging information selection screen 351 illustrated in FIG. 3(b) to be displayed.

Imaging information is selected in response to an operation input on the operation unit 110 with the screen being displayed. In response to the examination start button 357 being pressed, the display control unit 202 causes, for example, the imaging screen 401 illustrated in FIG. 4 to be displayed.

In response to receipt of an imaging prohibition signal, an urgent-imaging-instruction acceptance permission signal, or an imaging permission signal from the X-ray imaging apparatus 106 with the imaging information selection screen 351 illustrated in FIG. 3(b) and the imaging screen 401 illustrated in FIG. 4 being displayed, the display screen is updated. The imaging control unit 201 controls the display control unit 202 to update the state indications 360a, 360b, or 360c for the X-ray imaging apparatus 106 that is the transmission source of the signal. Even in the case where the screen is not displayed or there is no state display area for the X-ray imaging apparatus 106 from which the signal is received, the imaging control unit 201 updates information on the state of the X-ray imaging apparatus 106 from which the signal is received, and stores the information in the storage unit 108 for the X-ray imaging apparatus 106 from which the signal is received.

For example, before or after the imaging screen illustrated in FIG. 4 is displayed, the specifying unit 206 specifies imaging information selected first from among the selected pieces of imaging information. For example, in response to specifying of the imaging information, a transition signal for causing the X-ray imaging apparatus 106 to enter the imaging permitted state may be sent to the X-ray imaging apparatus 106.

When X-rays are radiated in response to the X-ray radiation switch 103 being pressed with the indication (first indication) indicating that imaging is permitted being displayed on the display unit 109 after the imaging permission signal is received, an X-ray image is captured by the X-ray imaging apparatus 106. At that time, in response to the X-ray irradiation detection unit 1062 detecting X-rays, the imaging information processing apparatus 107 receives a detection signal. In response to receipt of the detection signal, the display control unit 202 causes the display unit to display an indication indicating that X-rays have been detected. For example, as an indication indicating that X-rays are radiated at an appropriate timing, that is, in the imaging permitted state, a message such as "Irradiation of X-rays detected normally" may be displayed at that time.

The communication circuit 112 then receives an X-ray image from the X-ray imaging apparatus 106, and the image processing unit performs image processing, such as gradation conversion processing, contrast correction processing, noise reduction processing, artifact suppression processing, and MTF improving processing. The display control unit 202 causes the display unit 109 to display the X-ray image that has been subjected to the image processing. Before or after the image processing and the display processing, the next imaging information is specified by the specifying unit 206. The following processing is performed similarly.

Now, urgent imaging will be described below. The X-ray imaging apparatus 106 according to one of embodiments obtains, prior to imaging, dark current data or correction dark data for reducing or removing a dark current component that is superimposed on the X-ray image in some cases. In such cases, correction dark obtaining driving is performed after the stabilizing driving so as to accumulate electric charges in individual pixels of the X-ray sensor 1061 without the X-ray sensor 1061 being irradiated with X-rays and to read these electric charges.

Obtaining such correction dark is effective to appropriately perform dark current correction; however, it can be performed after imaging, for example. Accordingly, ordinary imaging is not permitted in the correction dark obtaining period, whereas urgent imaging is permitted. To enable this configuration, the X-ray imaging apparatus 106 outputs an urgent-imaging-instruction acceptance permission signal (third signal) in response to the start of obtaining the correction dark after the end of stabilizing driving. The communication circuit 112 of the imaging information processing apparatus 107 receives this acceptance permission signal, in response to which, the display control unit 202 causes the display unit 109 to display an indication indicating that urgent imaging is permitted. If urgent imaging is not triggered, the X-ray imaging apparatus 106 sends an imaging permission signal upon finishing obtaining the correction dark.

The imaging control unit 201 causes the communication circuit 112 to send an urgent instruction signal for instructing urgent imaging in response to an operation input for starting urgent imaging fed from the operation unit 110, for example. In response to receipt of this signal, the X-ray imaging apparatus 106 ends the correction dark obtaining driving and enters a state where X-ray imaging is permitted. In addition, the communication circuit of the X-ray imaging apparatus 106 sends an urgent permission signal (fourth signal) indicating that the X-ray imaging apparatus 106 has entered a state where urgent imaging is permitted.

In the case where urgent imaging is performed in this manner, correction is performed by using, in dark current correction processing, correction dark that is obtained in advance, such as at the time of shipment or immediately before the end of the last operation. Alternatively, in the case where urgent imaging is performed, the correction dark obtaining driving is performed subsequent to the X-ray imaging. The communication circuit of the X-ray imaging apparatus 106 sends the obtained correction dark after sending the X-ray image, and the imaging information processing apparatus 107 performs dark current correction. In this way, the correction processing can be performed more rapidly. Alternatively, the dark current correction is performed in the X-ray imaging apparatus 106 by using the obtained correction dark, and the corrected image data is sent to the imaging information processing apparatus 107. With such a configuration, urgent imaging can be handled and the usable period of the X-ray imaging apparatus can be increased. Thus, such a configuration is effective.

For example, even in the case where above-described urgent imaging is permitted, the control unit of the X-ray imaging apparatus 106 causes the X-ray irradiation detection unit 1062 to operate before the imaging permission signal (first signal) is sent, the urgent-imaging acceptance permission signal (third signal) is sent, or the urgent instruction signal is received. In addition, in response to the X-ray irradiation detection unit 1062 detecting irradiation of X-rays before the first and third signals are sent, the control unit of the X-ray imaging apparatus 106 causes an image obtained in response to the detection to be sent to the imaging information processing apparatus 106. This configuration makes it possible to detect irradiation of X-rays before urgent imaging is permitted. In addition, in this case, the display control unit 202 the display control unit 202 can display an indication corresponding to the image obtained in response to detection of irradiation of X-rays before urgent imaging is permitted. The user can be informed that an image has been obtained in response to irradiation of X-rays before urgent imaging is permitted.

Referring to FIG. 6(*b*), a flow of a process performed when irradiation of X-rays is detected before stabilizing driving will be described. A description of processing similar to that of FIG. 6 may be omitted.

The X-ray irradiation detection unit 1062 detects X-rays in a situation such as X-rays are radiated from the X-ray generation unit 102 during stabilizing driving or before stabilizing driving is started. In response to detection of irradiation of X-rays, the X-ray imaging apparatus 106 sends a detection signal to the imaging information processing apparatus 106. The X-ray imaging apparatus 106 then performs operations of accumulation, reading, and sending of an image as in the process illustrated in FIG. 6(*a*).

If the correction dark obtaining process has never been performed since the startup of the X-ray imaging apparatus 106, the X-ray imaging apparatus 106 then starts the correction dark obtaining process. In this way, an image on which dark current correction has been appropriately performed can be obtained even if the correction dark is not obtained before imaging. The correction dark may be sent from the X-ray imaging apparatus 106 to the imaging information processing apparatus 107 as illustrated in FIG. 6(*b*), or dark current correction may be performed using the correction dark and the corrected X-ray image may be sent to the imaging information processing apparatus 107.

In parallel to the above-described operation performed by the X-ray imaging apparatus 106, processing in the imaging information processing apparatus 107 is performed. In response to receipt of the detection signal from the X-ray imaging apparatus 106, the imaging control unit 201 refers to the state of the X-ray imaging apparatus 106 based on the information in the storage unit 108 and determines whether the current state is the imaging permitted state. Note that the X-ray imaging apparatus may send the detection signal that includes information indicating whether the current state is the imaging permitted state.

The imaging control unit 201 determines that X-rays have been detected in the image prohibited period. In response to the determination, the display control unit 202 causes the display unit 109 to display an indication (second indication) indicating that irradiation of X-rays has been detected in the imaging prohibited period as described by using FIG. 5(a) or FIG. 5(b), for example.

Then, in response to receipt of an X-ray image, the imaging control unit 201 causes the imaging processing unit to perform image processing. In the case where the X-ray image is an image on which dark current correction is not performed as illustrated in FIG. 6(b), for example, processing for reducing line or band noise resulting from dark current is performed. The processed image is displayed on the display unit 109 by the display control unit 202. Then, in response to receipt of correction dark, the image processing unit performs dark current correction, and the display control unit 202 displays the dark-current-corrected image in place of the image already displayed.

Here, the above-described indication (second indication) is kept displayed even after the X-ray image is received, display of the image is started, the image processing is performed, and the displayed image is updated. The first, second, and third buttons in FIG. 5(a), for example, can be pressed at a given timing with the second indication being displayed, and processing is performed on the image in response to pressing of any of the buttons.

Pressing the third button 503 makes it possible to utilize even an X-ray image obtained in an inappropriate period as an image used for making a diagnosis if the image quality is sufficiently high for use in making a diagnosis. In this way, an X-ray image obtained as a result of the subject being exposed to radiation can be effectively utilized.

In addition, in response to pressing of the first button 502 for setting the image as a failed image or the second button 503 for retaking, the imaging control unit 201 aborts processing, such as image processing and dark current correction, for example. This configuration allows the subsequent imaging operation to be performed rapidly.

Referring to a flowchart of FIG. 7, a flow of an imaging information processing process according to an embodiment will be described.

In S700, the communication circuit 112 receives, from the X-ray imaging apparatus 106, a detection signal (X-ray detection signal) indicating that irradiation of X-rays has been detected.

In S701, the imaging control unit 201 determines whether the X-ray imaging apparatus 106 is in the imaging permitted state at the time of receipt of the detection signal. The imaging control unit 201 makes the above-described determination based on information, for example, whether the imaging permission signal has been received, whether an indication (Ready indication) indicating that the X-ray imaging apparatus 106 is in the imaging permitted state is displayed by the display control unit 202, or whether the state information of the X-ray imaging apparatus 106 stored in the storage unit 108 indicates the imaging permitted state. If the current state is not the imaging permitted state, the process proceeds to step S702. If the current state is the imaging permitted state, the process proceeds to step S719.

Steps S702-S707 illustrate a flow of processing performed when the X-ray detection signal is received in the imaging prohibited state. In step S702, the display control unit 202 causes the display unit 109 to display a dialog indicating that the X-ray detection signal is received in the imaging prohibited state as illustrated in FIG. 5(b), for example. This display is continued until one of the buttons displayed on the dialog is pressed.

Then, in step S703, the communication circuit 112 receives an X-ray image. In step S704, the information generation unit 204 generates identification information indicating that the X-ray image is an image obtained in the imaging prohibited state, on the basis of the signal received from the X-ray imaging apparatus 106 such as the above-described detection signal or the X-ray imaging prohibition signal. The imaging control unit 201 associates the identification information and the X-ray image with each other, and temporarily stores the identification information together with the X-ray image in a temporary memory such as a RAM not illustrated. In step S705, the image processing unit of the imaging information processing apparatus performs image processing on the obtained image. In step S706, the display control unit 202 causes the display unit 109 to display the image-processed image. In step S707, the imaging control unit 201 determines whether the first button 502 of the warning indication 501, the second button 503 or the failed image button 429, or the retake button 428 is pressed with the image being displayed. The flowchart illustrated in FIG. 7 describes the case where either a failed image instruction or a retake instruction is given below. If an examination suspend instruction, an image output instruction, or an examination end instruction is given by pressing the examination suspend button 415, the image output button 416, or the examination end button 417, respectively, instead of the failed image instruction or the retake instruction, the processing of step S713 and subsequent steps is performed. Alternatively, if the third button 504 is pressed, the imaging information processing apparatus may enter a state for waiting for the examination suspend instruction, the image output instruction, and the examination end instruction. Alternatively, if there is imaging information for which imaging is not performed, the imaging information processing apparatus may enter a state where imaging corresponding to the imaging information can be performed.

In S708, the imaging control unit 201 determines which of a failed image instruction or a retake instruction is given if the failed image instruction or the retake instruction is given in S707. If the failed image instruction is given, the process proceeds to step S709. If the retake instruction is given, the process proceeds to step 715.

Steps S709-S712 describes processing performed in the case where the failed image instruction is given. In S709, the failed image setting unit 207 determines whether the image is already set as a failed image by referring to data stored in the storage unit 108. If the failed image setting is not made, the process proceeds to step S710, in which the failed image setting unit 207 sets the image as a failed image. In step S711, the failed image setting unit 207 also sets failed image reason information in response to an operation input from the operation unit 110. The image, the information indicating that the image is a failed image, and the failed image reason information are stored in the storage unit 108 in association with one another.

On the other hand, if it is determined in step S709 that the image is an image that is already set as a failed image, the failed image setting unit 207 cancels the failed image setting in step S712. Specifically, the failed image setting unit 207 rewrites data "1" indicating that the image is a failed image to data "0" indicating that the image is not a failed image and stores the data in the storage unit 108 in association with the image.

Then, in step S713, the imaging control unit 201 waits for input of an image output instruction given by pressing the image output button 416 or an examination end instruction given by pressing the examination end button 417. If there is an input, the imaging control unit 201 determines that an output instruction is given, and the process proceeds to step S714.

In S714, the image output control unit 208 controls the communication circuit 112 so as to send an X-ray image that is not set as a failed image to the PACS 115. After the output completes, the process ends.

Steps S715-S718 describe processing performed in the case where a retake instruction is given. Here, a retaking process is a process of generating imaging information for retaking after setting the image as a failed image. In step S715, the failed image setting unit 207 sets the image as a failed image. In the case where retaking is instructed, the failed image setting unit 207 maintains the failed image setting even when there is an image already set as a failed image and does not cancel the failed image setting. As in step S711, in step S716, the failed image setting unit 207 sets the failed image reason information in response to an operation input from the operation unit 110 and stores the failed image reason information in the storage unit 108 in association with the image.

In S717, the imaging control unit 201 generates imaging information including the same imaging condition, the same imaging processing condition, and the same output condition as the imaging condition for the image. The imaging control unit 201 stores the generated imaging information in the storage unit 108 in association with the same examination information as that of the imaging information set as the failed image. In step S718, the display control unit 202 additionally displays the newly generated imaging information in the imaging information display area 408.

S719-S723 illustrate a flow of processing performed when a detection signal is received in the imaging permitted state. In S719, the display control unit 202 displays a dialog indicating that an X-ray detection signal is received in the imaging permitted state so as to be superimposed on the imaging screen 401 or the like. In S720, the communication circuit 112 receives an X-ray image from the X-ray imaging apparatus 106. In step S721, the image processing unit of the imaging information processing apparatus performs image processing on the X-ray image. In step S722, the display control unit 202 causes the display unit 109 to display the image-processed X-ray image.

In S723, the imaging control unit 201 determines, for example, whether the failed image button 429 or the retake button 428 in FIG. 4 is pressed in accordance with a detection result supplied from the input detection unit 203. If it is determined that the failed image button 429 or the retake button 428 is pressed, the above-described processing of step S708 and the following steps is performed. If it is determined that neither buttons are pressed, the above-described processing of step S713 and the following steps is performed.

Figure 8:
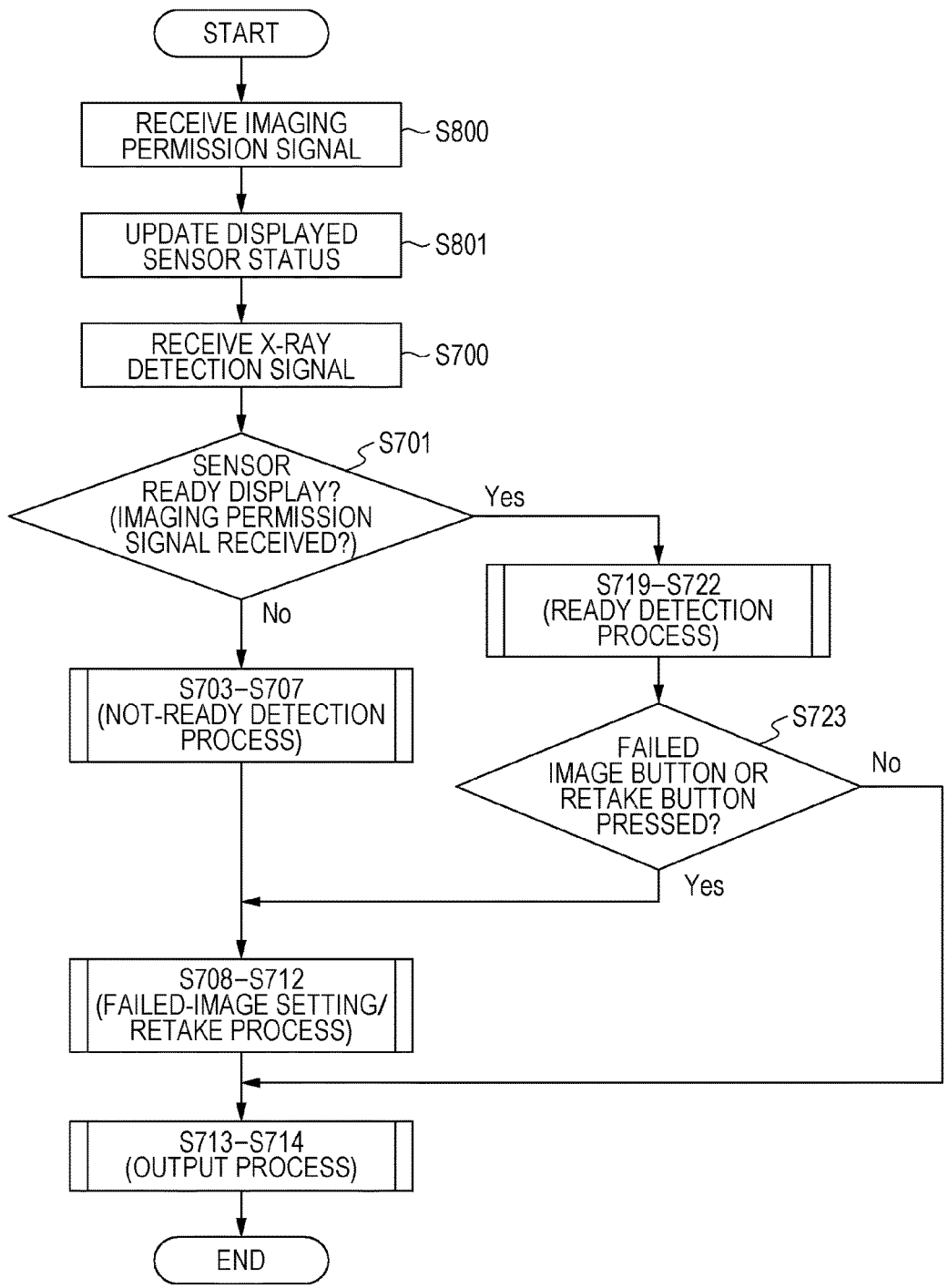
FIG. 8 is a flowchart illustrating a flow of an imaging information processing process in another embodiment.

Referring to a flowchart of FIG. 8, provided is a flowchart illustrating a flow of an imaging information processing process according to another embodiment.

In S800, the communication circuit 112 receives an imaging permission signal from the X-ray imaging apparatus 106. In response to the reception, the imaging control unit 201 updates the state information of the X-ray imaging apparatus 106 stored in the storage unit 108. In S801, the display control unit 202 also updates the state indication on the imaging screen 401 or the imaging information selection screen 351 to an indication such as "Ready" indicating a state where imaging is permitted.

In step S701, the imaging control unit 201 determines whether the X-ray imaging apparatus 106 is in the imaging permitted state. There may be a case where the X-ray imaging apparatus 106 is not in the imaging permitted state due to a reason such as a subsequent change in the state of the X-ray imaging apparatus 106 or occurrence of a failure even if the imaging permission signal is received in step S800. Accordingly, even in the case where the imaging permission signal is received, the determination processing of S701 is performed.

For example, the X-ray imaging apparatus 106 and the imaging information processing apparatus 107 perform communication on a regular basis via the communication circuit 112. When such regular communication stops, the imaging control unit 201 updates the state information of the X-ray imaging apparatus 106 stored in the storage unit 108 to a state, such as "occurrence of a failure". In this way, the imaging information processing apparatus 107 can more appropriately manage the state of the X-ray imaging apparatus 106.

Figure 7:
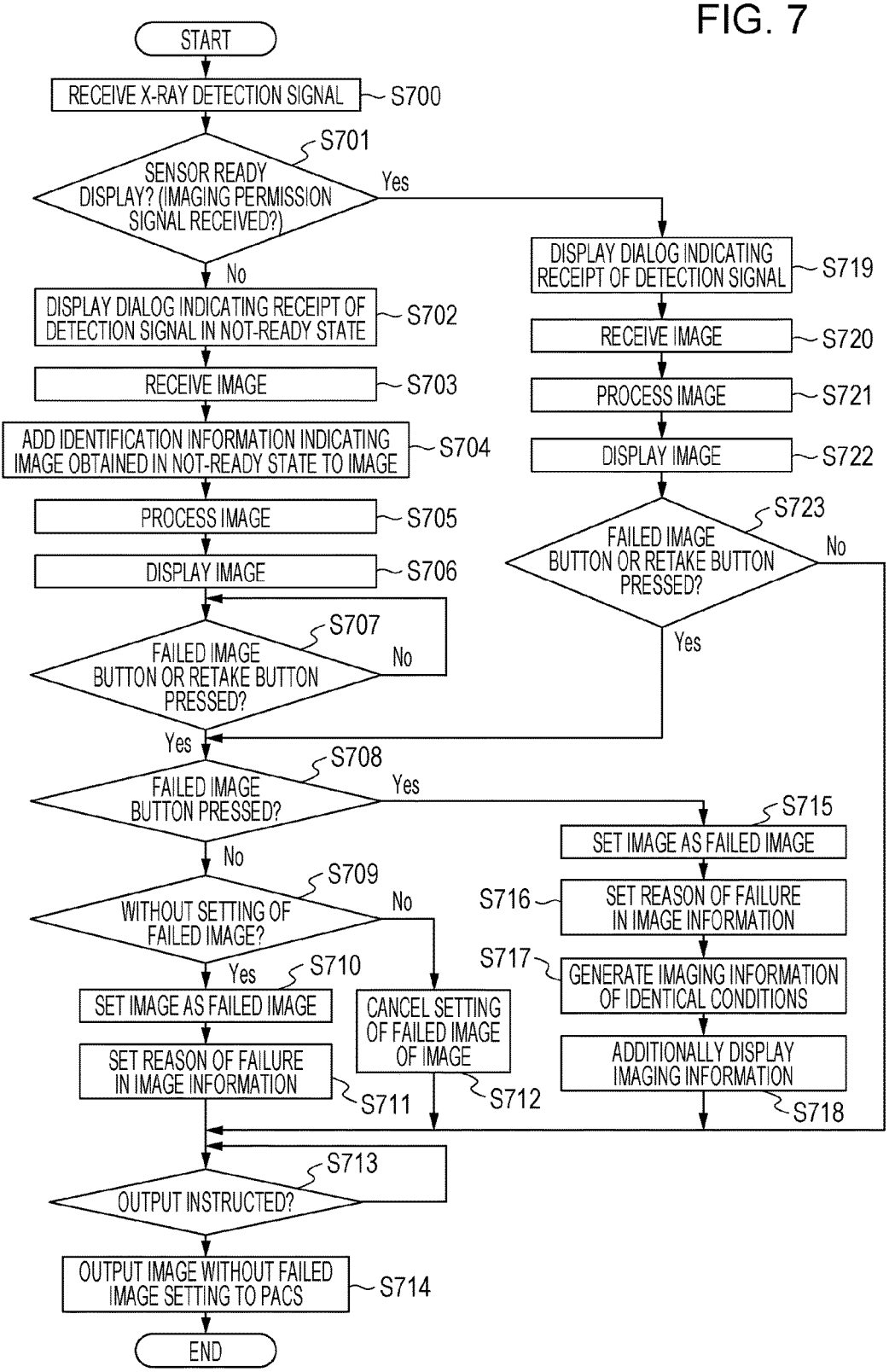
FIG. 7 is a flowchart illustrating a flow of an imaging information processing process in the embodiment.

Processing in S703-S707 performed in response to detection of X-rays in the imaging prohibited state, failed image or retaking processing in S708-S712, output processing in S713-S714, processing in S719-S722 performed in response to detection of X-rays in the imaging permitted state, and other processing have a flow that is similar to that of the processing described in FIG. 7.

FIG. 9(a) is a flowchart illustrating a flow of image data after detection in another embodiment. Upon irradiation of X-rays being detected by the X-ray irradiation detection unit 1062 of the X-ray imaging apparatus 106 in S901, an X-ray image is accumulated in S902 and is obtained. After image processing in S903, the image is stored in the image storage unit of the X-ray imaging apparatus 106. The stored image is kept stored until preparation for obtaining an image completes in the imaging information processing apparatus 107. The imaging information processing apparatus 107 enters the imaging permitted state after preparation for obtaining an image completes in response to input of information, such as the patient information and the examination procedure. At that time, it may be determined whether the current state is the imaging permitted state based on a timing at which capturing of an image permitted, depending a time elapsed from the previous refresh driving. Information necessary for the determination may be received from the X-ray imaging apparatus 106. In this case, control is performed by the X-ray imaging apparatus 106 such that the imaging information processing apparatus 107 does not enter the imaging permitted state during the preparation period.

Alternatively, it may be determined whether the current state is the imaging permitted state in accordance with the state of communication between the imaging information processing apparatus 107 and the X-ray imaging apparatus 106. Whether the imaging permitted state or not may be switched depending on whether an operation is performed in the imaging information processing apparatus 107. In either case, the imaging permitted state is a state where an image can be securely received immediately after imaging is performed, and a period of the imaging permitted state is the imaging permitted period. Conversely, a period for which secure imaging is not performed is the imaging prohibited state, and a period thereof is the imaging prohibited period.

Once the imaging information processing apparatus 107 enters the imaging permitted state, the X-ray imaging apparatus 106 is notified that the imaging information processing apparatus 107 is in the imaging permitted state. In response to the notification, the X-ray imaging apparatus 106 transfers information stored in the image storage unit of the X-ray imaging apparatus 106 to the imaging information processing apparatus 107 (S904). The imaging information processing apparatus 107 is already fed with the patient information and other information to be associated with an image captured next, and the transferred image is associated with this information and stored in the storage unit 108.

The transferred image is displayed on the display unit 109 by the display control unit 202. If the image quality of the image is not sufficient to be used in making a diagnosis, the image is discarded through the failed image processing or the like as described above, and retaking is performed using the same conditions.

The X-ray imaging apparatus 106 may attach at least an image captured in response to detection of irradiation of X-rays in a detection mode 1, with information indicating that the image is an image obtained as a result of radiation in an appropriate period. This information may be written in image data as a header of the image data or may be stored as a file separately from the image data. In the case where image information attached with such information is transferred, the display control unit 202 displays, together with the image, a dialog indicating that the image has been captured at an inappropriate radiation timing. In this way, a radiographer's attention can be drawn. The operator can then determine whether the image information is necessary, such as whether to set the image as a failed image. With such a configuration, an X-ray image can be obtained also in response to radiation in the preparation period, and the image can be managed by associating appropriate information to the image.

FIG. 9(b) is a flowchart illustrating a flow of image data after the detection in another embodiment.

In this embodiment, upon the imaging information processing apparatus 107 becoming ready to obtain the image, the image information that has been captured and stored in the image storage unit of the X-ray imaging apparatus 106 is transferred to the imaging information processing apparatus 107. The failed image setting unit 207 of the imaging information processing apparatus 107 that has received the image information automatically processes the image as a failed image without displaying the image. In the failed image processing, the failed image setting unit 207 may record a reason indicating that the image was captured at an inappropriate radiation timing. At the same time, the display control unit 202 may display a dialog indicating that radiation is performed at an inappropriate timing. By associating information such as the patient information and the imaging conditions with the image information processed as a failed image, a radiation dose of the patient can be appropriately managed. Further, the image can be utilized as an image used for making a diagnosis by cancelling the failed image setting.

As for the next imaging, the imaging information processing apparatus 107 gets ready for retaking based on the same conditions used for the image processed as a failed image. As described above, automatically processing an image as a failed image can reduce the processing by the operator and preparation for next imaging can be completed rapidly, and thus can improve the workflow.

Referring to FIG. 10, the X-ray imaging apparatus 106 according to the embodiment of the present invention will be described. Based on FIG. 10(a), a configuration of the X-ray imaging apparatus 106 will be described. The X-ray imaging apparatus 106 includes the X-ray sensor 1061 configured to obtain an X-ray image, the X-ray irradiation detection unit 1062 configured to detect irradiation of X-rays based on an output of the X-ray sensor 1061, a driving circuit 1007 configured to drive the X-ray sensor 1061, a communication circuit 1063 configured to send, to the imaging information processing apparatus 107, the X-ray image and the imaging permission signal indicating that the X-ray imaging apparatus 106 has entered the state where irradiation of the X-ray sensor 1061 with X-rays is permitted, and an imaging control unit 1011. The imaging control unit 1011 causes the X-ray irradiation detection unit 1062 to operate before the imaging permission signal is sent. The imaging control unit 1011 also causes the communication circuit 1063 to send the X-ray image to the imaging information processing apparatus 107, in response to the X-ray irradiation detection unit 1062 detecting irradiation of X-rays before the imaging permission signal is sent. In this way, detection of irradiation before the imaging permission signal is sent is handled. In addition, even in the case where the obtained image is highly likely to have an insufficient image quality, the image is sent to the imaging information processing apparatus 107 in consideration of a possibility of reuse because the image is an X-ray image obtained as a result of exposure to radiation. The X-ray sensor 1061 includes a two-dimensional imaging element 1005 and a bias power supply 1006. The X-ray imaging apparatus 106 includes a reading circuit 1008 for reading image data, an image processing unit 1009 for processing the read image, an image storage unit 1010, and the communication circuit 1063 for communicating with the imaging information processing apparatus 107 or the like that resides outside for control. A housing 1012 of the X-ray imaging apparatus 106 contains the above-described units. The X-ray imaging apparatus 106 has a substantially rectangular parallelepiped shape.

The two-dimensional imaging element 1005 includes pixels arranged in a two-dimensional matrix, the pixels including a plurality of solid-state photoelectric converter elements. The bias power supply 1006 is a power supply for supplying a bias voltage to the two-dimensional imaging element 1005. The X-ray irradiation detection unit 1062 is a detection unit that is connected to, for example, the bias power supply 1006 and that detects irradiation of X-rays. The imaging control unit 1011 controls various operations of the X-ray imaging apparatus.

102 denotes an X-ray generation unit. On/Off of X-rays and X-ray generation conditions such as tube current and tube voltage are controlled by the X-ray control apparatus 104. The X-ray generation unit 102 can generate pulsed X-rays 220.

A subject 300 is irradiated with the X-rays 220 generated by the X-ray generation unit 102. The X-rays 220 that have passed through the subject 300 are incident onto the two-dimensional imaging element 1005 disposed inside the X-ray imaging apparatus 106 and are converted into an X-ray image. The X-ray image is read via the reading circuit 1008, is subjected to image processing, and then is stored in the image storage unit 1010. The image storage unit 1010 has a storage capacity capable of storing image data of at least one image. The image data that has been stored in the image storage unit 1010 is sent to the outside via the communication circuit 1063. Transmission to the outside may be performed simultaneously with storage; however, it is desirable to store the entire data in the image storage unit until the entire image data is successfully sent because the image data can be re-sent in the case where the external imaging information processing apparatus 107 or the like fails to reproduce the correct image due to a failure in transmission of part of the image data resulting from a bad communication state, for example.

The storage control unit 205 stores the transferred image in the storage unit 108, and the display control unit 202 displays the transferred image on the display unit 109. The communication circuit 1063 may perform wired communication or wireless communication. In addition, the transferred image may be stored directly in the storage unit 108 without via the imaging information processing apparatus 107. Alternatively, the X-ray imaging apparatus 106 may include a storage unit therein and may store the image data in the storage unit.

FIG. 10(*b*) is an equivalent circuit diagram of the X-ray sensor 1061.

The two-dimensional imaging element 1005 includes a plurality of pixels 1051 arranged in a matrix of m rows and n columns. To simplify the description, FIG. 10(*b*) illustrates a 3×3 matrix, where m=3 and n=3; however, the detection device actually used includes many pixels of m=2800 and n=2800, for example. Each pixel includes a scintillator (not illustrated) that converts the X-rays 300 into light of a spectrum band sensible by the photoelectric converter element, the photoelectric converter element (S11 to S33), and a switch element (T11 to T33).

The photoelectric converter element generates and accumulates electric charges based on an amount of incident X-rays. X-rays that have passed through the subject 300 have a distribution that is dependent on X-ray transmission quantities that are different for structures, such as bones and internal organs, and a lesion in the subject. Thus, such structures are converted into a distribution of electric charges, and the electric charges are accumulated.

As a photoelectric converter element, various elements including amorphous silicon or polysilicon are known in addition to a CCD. In this embodiment, a MIS photodiode including, as a main material, amorphous silicon disposed on an insulating substrate such as a glass substrate is used as the photoelectric converter element; however, a PIN photodiode may be used. In addition, a direct converter element that directly converts radiation into electric charges can be suitably used.

As the switch element, a transistor having a control terminal and two main terminals is suitably used. In this embodiment, a thin-film transistor (TFT) is used.

In FIG. 10(*b*), a lower-side electrode of the photoelectric converter element is denoted by G, and an upper-side electrode thereof is denoted by D. The D electrode is electrically connected to one of two main terminals of the switch element, whereas the G electrode is connected to the bias power supply 1006 via a bias line. The control terminals of the plurality of switch elements (for example, T11 to T13) arranged along the row direction are connected in common to a first-row driving line g1 and are supplied, via the driving line from the driving circuit, with a driving signal for controlling the conduction state of the switch elements on a line-by-line basis.

The main terminals, which are not connected to the photoelectric converter elements, of the plurality of switches (for example, T11 to T31) arranged along the column direction are electrically connected to a first-column signal line s1. While the switch element is in the conductive state, an electric signal according to the amount of electric charges accumulated in the photoelectric converter element is output to the reading circuit 1008 via the signal line. The plurality of signal lines (s1 to s3) arranged along the column direction transfer the corresponding electric signals read from a plurality of pixels to the reading circuit 1008 in parallel.

The reading circuit 1008 includes a multiplexer (not illustrated) that sequentially processes the electric signals read in parallel and outputs a resulting serial image signal, and a buffer amplifier (not illustrated) that performs impedance conversion on the image signal and outputs the resulting image signal. The image signal that is an analog electric signal output from the buffer amplifier is converted into digital image data by a first A/D converter 1052.

The bias power supply 1006 supplies the G electrode of the photoelectric converter element with a bias voltage Vs via the bias line and outputs current information containing a change in an amount of current supplied to the bias line. In the embodiment, a current-voltage conversion circuit including an operational amplifier AMP and a resistor R and a second A/D converter 1054 that converts the resulting output voltage into a digital value are used as a circuit that output the current information; however, the configuration is not limited to this one. For example, a current-voltage conversion circuit that uses a shunt resistor may be used. In addition, the output voltage of the current-voltage conversion circuit may be output without processing it. Further, a physical quantity corresponding to the amount of current supplied to the bias line Bs may be output.

The current information on the bias line is sent to the X-ray irradiation detection unit 1062 and is used to detect irradiation of X-rays by detecting a change in the amount of current that occurs during irradiation of X-rays.

The bias power supply 1006 also includes a refresh power supply Vr. Like Vs, Vr is also connected to the G electrode of each photoelectric converter element via the bias line, and Vr is applied to the G electrode for a refresh period of the photoelectric converter element. The voltage applied to the G electrode is controlled by a SW control circuit 1053. Control is performed such that Vr and Vs are applied during the refresh period and a period other than the refresh period, respectively.

Figure 11:
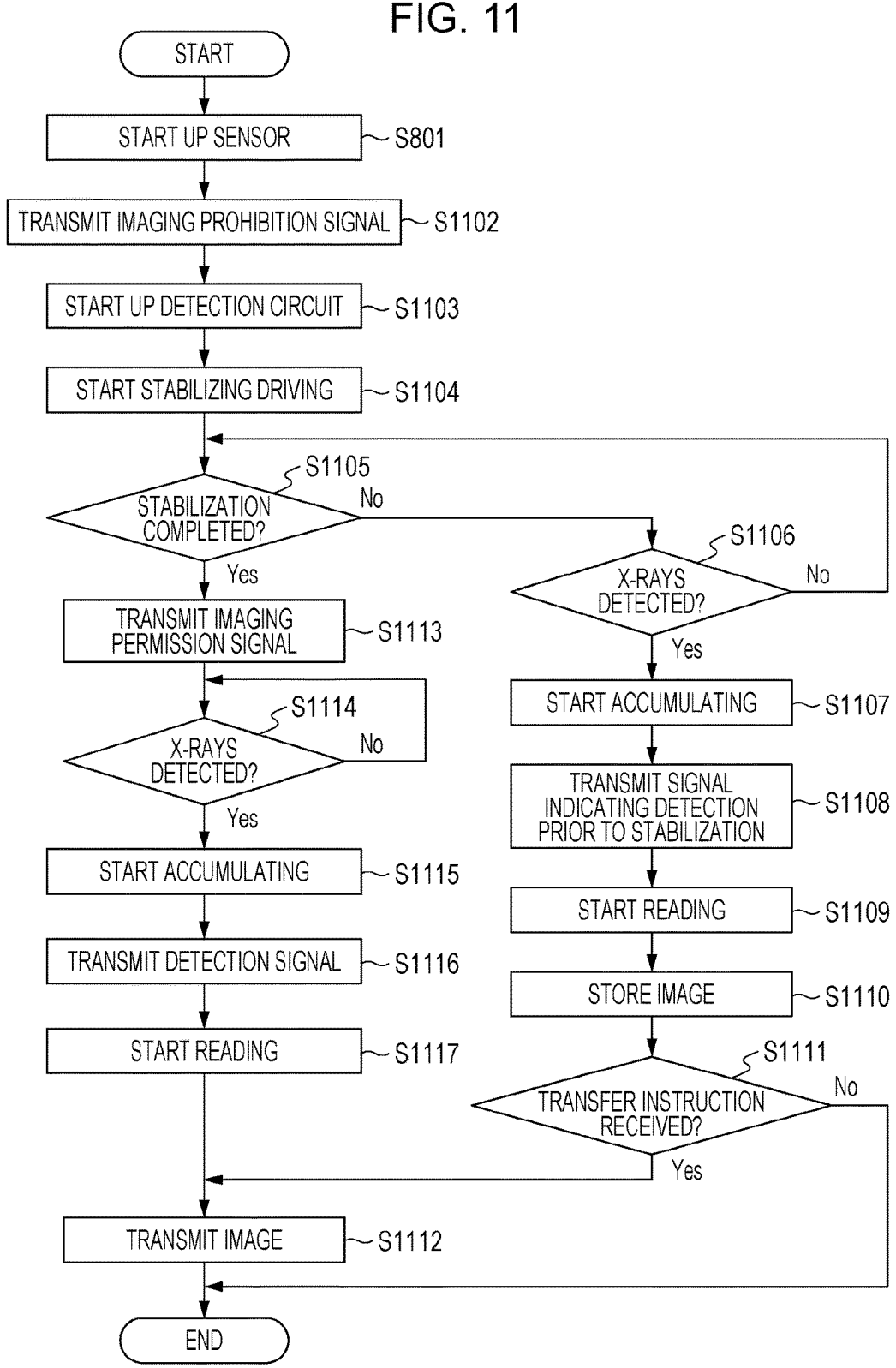
FIG. 11 is a flowchart illustrating a flow of a control process performed by the X-ray imaging apparatus according to the embodiment.

By using a flowchart of FIG. 11, a flow of a control process performed by the X-ray imaging apparatus according to the embodiment will be described.

In S1101, the imaging control unit 1011 of the X-ray imaging apparatus 106 starts up the X-ray sensor 1061. Specifically, the imaging control unit 1011 supplies power to the bias power supply 1006 to start up a DC/DC converter of the bias power supply 1006 and causes the DC/DC converter to generate a bias voltage to be applied to the two-dimensional imaging element 1005. In step S1102, the communication circuit 1063 of the X-ray imaging apparatus 106 sends an imaging prohibition signal to the communication circuit 112 of the imaging information processing apparatus 107. In step S1103, the imaging control unit 1011 supplies power to the X-ray irradiation detection unit 1062 and the second A/D converter 1054 to exert the X-ray detection function. In step S1104, the imaging control unit 1011 causes the driving circuit 1007 to operate and start stabilizing driving of the two-dimensional imaging element 1005. Specifically, the imaging control unit 1011 causes accumulation and output of electric charges to be repeatedly performed on a regular basis, and then stands by for a certain period.

In S1105, the imaging control unit 1011 determines whether stabilizing driving has completed. If stabilizing driving has not completed, the process proceeds to processing of S1106 and the following steps. If stabilizing driving has completed, the process proceeds to processing of S1113 and the following steps.

In step S1106, the imaging control unit 1011 determines whether irradiation of X-rays has been detected on the basis of a determination signal supplied from the X-ray irradiation detection unit 1062. If irradiation is detected, the process proceeds to processing of step S1107 and the following steps. If irradiation is not detected, the process returns again to the determination process of determining whether stabilization has completed in step S1105.

In step S1107, the imaging control unit 1011 controls the driving circuit 1007 to cause the two-dimensional imaging element 1005 to start accumulation. Specifically, the imaging control unit 1011 causes the TFT switches T11 to T33 to enter the off state so as to allow the photoelectric converter elements S11 to S33 to accumulate electric charges based on the X-rays. In step S1108, the imaging control unit 1011 causes the communication circuit 1063 to send a signal indicating that irradiation of X-rays has been detected before stabilization completes. Immediately after the sending, the imaging control unit 1011 causes the driving circuit 1007 to operate so as to sequentially perform reading on pixels of the two-dimensional imaging element 1005. Specifically, the imaging control unit 1011 sequentially makes the TFT switches T11 to T33 to the on-state. In parallel to this, the imaging control unit 1011 starts up the reading circuit 1008 and the first A/D converter 1052, amplifies the electric signal output from the two-dimensional imaging element 1005, and obtains digital X-ray image data with the first A/D converter 1052. The obtained image data is subjected to, for example, dark current correction, gain correction, and defective pixel correction by the image processing unit 1009. In step S1110, the image storage unit 1010 stores the obtained image.

In step S1111, the imaging control unit 1011 determines whether an image transfer instruction signal is received from the imaging information processing apparatus 107. Such a transfer instruction signal is a signal which the communication circuit 112 of the imaging information processing apparatus 107 sends to the communication circuit 1063 of the X-ray imaging apparatus 106 in response to pressing of the transfer button 506 illustrated in FIG. 5(b), for example. If it is determined that the transfer instruction signal is received, the process proceeds to step S1112, in which the communication circuit 1063 sends the X-ray image. If the transfer instruction signal is not received for a certain period, if next imaging is triggered without receiving the transfer instruction signal, or if a discard instruction signal that is sent by the imaging information processing apparatus 107 in response to pressing of the discard button 508 is received, the imaging control unit 1011 ends the process without performing step S1112.

As described above, the X-ray imaging apparatus 106 sends, to the imaging information processing apparatus 107, a signal indicating whether irradiation of X-rays has been detected before or after completion of stabilization, together with information indicating that irradiation with X-rays has been detected. In this way, the imaging information processing apparatus 107 determines whether an inappropriate image is highly likely to be obtained and can change the subsequent processing.

In addition, an X-ray image obtained in response to detection of irradiation of X-rays before stabilization completes is transferred only when a transfer instruction is received from the imaging information processing apparatus 107. In this way, the subsequent processing can be performed more rapidly by not sending inappropriate images.

Steps S1113-S1117 describe the flow of processing performed after stabilization has completed.

In step S1113, the communication circuit 112 sends the imaging permission signal to the imaging information processing apparatus 107. In step S1114, the imaging control unit 1011 determines whether X-rays have been detected as in S1106. If X-rays have been detected, the process proceeds to S1115. If X-rays have not been detected, determination in S1114 is repeatedly performed. In S1115, the imaging control unit 1011 causes the two-dimensional imaging element 1005 to enter the accumulation state as in S1107. In S1116, the imaging control unit 1011 causes the communication circuit 1063 to send a detection signal indicating that irradiation of X-rays has been detected after completion of stabilization. In S1117, the imaging control unit 1011 starts the read operation as in S1109. Thereafter, in S1112, the imaging control unit 1011 causes the communication circuit 1063 to output the X-ray image. In this case, it is considered that an appropriate image is obtained, thus the X-ray image is output without waiting for a transfer instruction.

Now, a method for detecting irradiation of X-rays in accordance with the embodiment will be described.

The above-described current information on the bias line can be used to detect irradiation of X-rays without processing the current information. The start of irradiation of X-rays can be identified by determining that a sampled current value input to the X-ray irradiation detection unit 1062 has exceeded a certain threshold. When the threshold is set low, irradiation can be detected in a short period from the start of irradiation; however, such a detection scheme is weak to an impact or magnetic noise and may cause an erroneous detection (state where irradiation is detected even if X-rays are not radiated). On the other hand, when the threshold is set high, a risk of erroneous detection due to noise reduces but the detection timing of irradiation of X-rays becomes late. If the period from the start of irradiation of X-rays to the detection is long, an artifact may occur in an image. Thus, it is preferable to make the period from the start of irradiation to the determination short. An optimum value of the detection threshold may be determined by taking these points into account.

Figure 12:
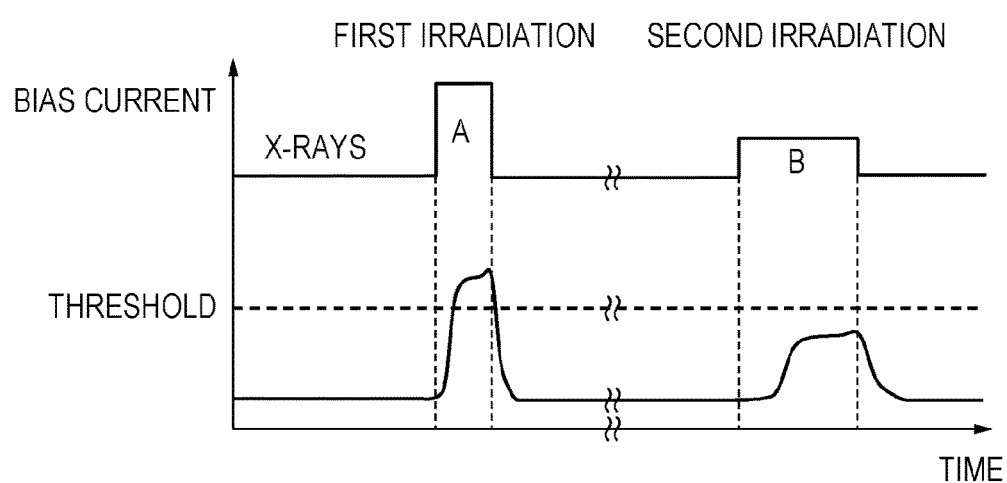
FIG. 12 is a diagram schematically illustrating a change in current information output by the X-ray sensor according to the embodiment when the X-ray sensor is irradiated with X-rays.

However, when detection is performed by using the current information without any processing, an issue that the detection performance changes depending on the incident amount of X-rays per unit time arises. FIG. 12 is a diagram schematically illustrating a change in current information on the bias line when X-rays are radiated. FIG. 12 illustrates a state where X-rays are radiated twice. Areas A and B respectively for the first irradiation and the second irradiation are the same, and thus there is no difference in contrast of the obtained image (identical images can be obtained). On the other hand, a period of X-ray irradiation is shorter in the first imaging than in the second imaging. This indicates that X-rays are output at a higher tube current in the first irradiation (it is assumed the tube voltages are equal). Referring to a change in the bias current at that time, the peak value for the first irradiation is higher than that for the second irradiation. Accordingly, when the threshold is set as indicated by a dashed line, the first irradiation is successfully detected but the second irradiation is not successfully detected in some cases. Some X-ray generation units are incapable of generating a high tube current, and detection may fail for a combination with such generation apparatuses.

Figure 13:
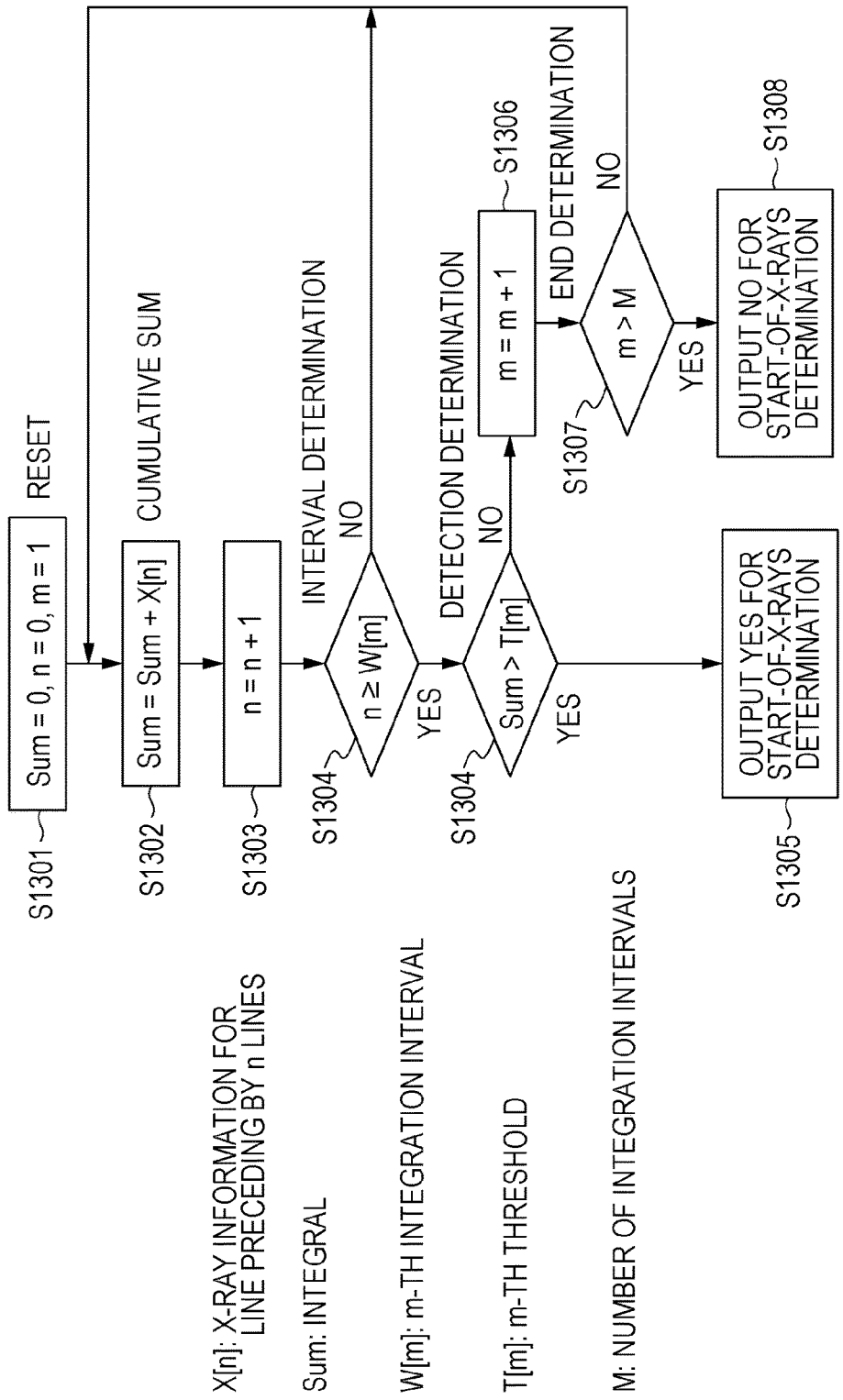
FIG. 13 is a flowchart illustrating a flow of a process performed by an X-ray irradiation detection unit according to the embodiment.

To address such issues, the start of X-ray irradiation is determined by integrating a sampled value X[N] of the current information on the bias line in this embodiment. FIG. 13 illustrates a flowchart of determining the start of X-ray irradiation.

First, Sum which is an integral, n which is an index of the sampled value, and m which is the number assigned to the integration interval are respectively given initial values. The initial values are set such that Sum=0, n=0, and m=1. This is called resetting the integrator. Then, a value obtained by adding the integral Sum and X[n] which is a sampled value for a line preceding by n is set as a new integral Sum, i.e., Sum=Sum+X[n]. After such adding, n=n+1 is performed, and then determination is performed for the interval. In the determination concerning the interval, while the index n of the sampled value does not exceed a pre-specified m-th integration interval W[m] (NO), adding is performed again. If the index n of the sampled value exceeds W[m] (YES), determination concerning detection is performed. In the detection determination, if the integral Sum exceeds a threshold T[m] of the pre-specified m-th interval (YES), information indicating the start of irradiation of X-rays is output. If the integral Sum does not exceed the threshold T[m] of the m-th interval (NO), m=m+1 is performed, and then determination concerning ending is performed. In the end determination, if the number m assigned to the integration interval does not exceed the number of integration intervals M (NO), adding is performed again. If m exceeds M (YES), X-ray information indicating that X-rays are not started is output.

Typically, M is a value of 1 or greater. The larger M is, the wider a range of a detectable irradiation condition becomes. When the integration interval is small, a range of handled imaging conditions for a high output and a short irradiation period increases. Conversely, when the integration interval is large, a range of handled imaging conditions for a low output and a long irradiation period increases. Because the irradiation conditions successfully handled change depending on the setting of the integration interval, almost all of necessary irradiation conditions can be handled by setting a plurality of integration intervals at an appropriate width.

In addition, the threshold T[m] for each integration interval may be constant regardless of the number m assigned to the integration interval or may be set to an optimum value for each integration interval. Typically, it is desirable to set an optimum value depending on an amount of noise contained in an electric signal, the amount of noise changing from integration interval to integration interval. For example, a standard deviation of the amount of noise is measured in advance, and an integer multiple of the standard deviation can be set as the threshold.

For example, an operation of the case where the number of integration intervals M is 4, a first integration interval W[1]=8, a second integration interval W[2]=16, a third integration interval W[3]=32, and a fourth integration interval W[4]=64 will be described in detail.

First, Sum which is the integral, n which is the index of the sampled value, and m which is the number assigned to the integration interval are given initial values. The initial values are set such that Sum=0, n=0, and m=1. Then, a value obtained by adding together the integral Sum and X[0] which is a sampled value preceding by 0 is set as a new integral Sum, i.e., Sum=Sum+X[0]. After such adding, the index of the sampled value is incremented such that n=n+1, and then the interval determination is performed. Because the index of the sampled value after the first addition is n=1, the index does not exceed the first integration interval W[1]=8. That is, NO is obtained in the interval determination, and thus adding is performed again. After the adding is performed eight times, the integral Sum stores a value obtained by integrating eight sampled values. In addition, because the index of the sampled value is n=8, the index exceeds the first integration interval W[1]=8. That is, YES is obtained in the interval determination, and thus the detection determination is performed. In the detection determination, when the integral Sum does not exceed a pre-specified threshold T[1] of the first interval, the number assigned to the integration interval is incremented such that m=m+1, and then the end determination is performed. Because the number assigned to the integration interval after the first detection determination is m=1, the number does not exceeds the number of integration intervals M=4. That is, NO is obtained in the end determination, and thus adding is performed again after m=m+1 is performed. When adding is performed 64 times without the integral Sum never exceeding the threshold T[m] for all integration intervals, the number assigned to the integration interval is m=4, and YES is obtained in the end termination. In this case, X-ray information indicating that X-rays are not started is output.

Conversely, when the integral Sum exceeds the threshold T[m] in the detection determination described above, the X-ray signal indicating the start of irradiation of X-rays is output at that time.

A configuration for performing detection determination for a plurality of integration intervals by using one integrator has been described above; however, a configuration may be made so that, by preparing M integrators for the number of integration intervals M, detection determination is performed in parallel by using the integrators.

In addition, a configuration in which the start of irradiation of X-rays is detected when the integral Sum exceeds the threshold in any one of the integration intervals has been described above; however, it may be determined that irradiation is started when the integral Sum exceeds the threshold in a plurality of integration intervals.

An operation of the photoelectric converter element will be described next. The photoelectric converter element has two operation modes, i.e., a refresh mode and a photoelectric conversion mode. FIG. 15(a) is a diagram schematically illustrating a cross-section of the photoelectric converter element of the embodiment. Layers of various materials are stacked on a glass substrate 1500 formed of an insulating base, thereby forming the photoelectric converter element. An upper electrode 1505 is formed as a transparent electrode, whereas a lower electrode 1501 is formed of Al or Cr, for example. An insulating layer 1502 is formed of amorphous silicon nitride and prevents both electrons and holes from pass therethrough. An intrinsic semiconductor layer 1503 is formed of hydrogenated amorphous silicon, generates electron-hole pairs when light is incident thereon, and functions as a photoelectric converter layer. A doped semiconductor layer 1504 is formed of n-amorphous silicon and functions as a hole blocking layer that prevents holes from entering the intrinsic semiconductor layer 1503.

FIG. 15(b) is an energy band diagram of the photoelectric converter element, part (a) illustrates a non-biased state, part (b) illustrates a state in the photoelectric conversion mode, and part (d) illustrates a state in the refresh mode. In the photoelectric conversion mode, a bias voltage Vs that makes the upper electrode have a positive voltage is applied across the upper electrode 1505 and the lower electrode 1501 as illustrated in part (b). The bias voltage Vs causes electrons in the intrinsic semiconductor layer to be discharged from the upper electrode 1505. On the other hand, implantation of holes into the intrinsic semiconductor layer 1503 from the upper electrode 1505 is attempted; however, holes are blocked by the doped semiconductor layer 1504 and cannot move to reach the intrinsic semiconductor layer 1503.

When light is incident onto the intrinsic semiconductor layer 1503 in this state, electron-hole pairs are generated by the photoelectric conversion effect. Electrons and holes move in the intrinsic semiconductor layer in accordance with the electric field without recombining together. The electrons are discharged from the upper electrode, whereas the holes are blocked by the insulating layer 1502 and stays at the interface.

When holes remaining at the interface of the insulating layer 1502 increases as a result of continuation of the photoelectric conversion operation, the electric field applied to the intrinsic semiconductor layer 1503 weakens because of the influence of the holes. As a result, electron-hole pairs generated by incident light recombine and disappear without moving in accordance with the electric field, and the photoelectric converter element loses the sensitivity to light. Part (c) illustrates the energy band diagram of this state. Such a state is called saturation.

To recover the sensitivity of the saturated photoelectric converter element, an operation called refreshing is performed. In the refresh mode, a refresh voltage Vr that gives the lower electrode a positive voltage is applied across the upper electrode 1505 and the lower voltage 1501 as illustrated in part (d). In the refresh mode, the holes remaining at the interface of the insulating layer are discharged from the upper electrode 1505, and instead of the holes, electrons are implanted and remains at the interface of the insulating layer.

If the operation mode is switched again to the photoelectric conversion mode at that time, the implanted electrons are rapidly discharged from the upper electrode, and the bias voltage is applied. Consequently, the photoelectric converter element regains the sensitivity to light.

As described above, the photoelectric converter element needs to be operated in the refresh mode on a regular basis to maintain the sensitivity to light. Refreshing is needed immediately after incidence of light, which corresponds to immediately after irradiation of X-rays. That is, the X-ray imaging apparatus needs to be operated in the refresh mode to get ready to the next imaging when X-rays are radiated and an X-ray image is obtained, thereby recovering the sensitivity. In addition, even in a state where X-rays are not radiated, electric charges (dark current) are unintentionally generated inside the photoelectric converter element due to the influence of temperature or other factors. The photoelectric converter element gradually loses the sensitivity due to accumulation of electric charges unintentionally generated in this manner. Thus, refreshing needs to be performed when the no irradiation state has lasted for a certain period.

Figure 16:
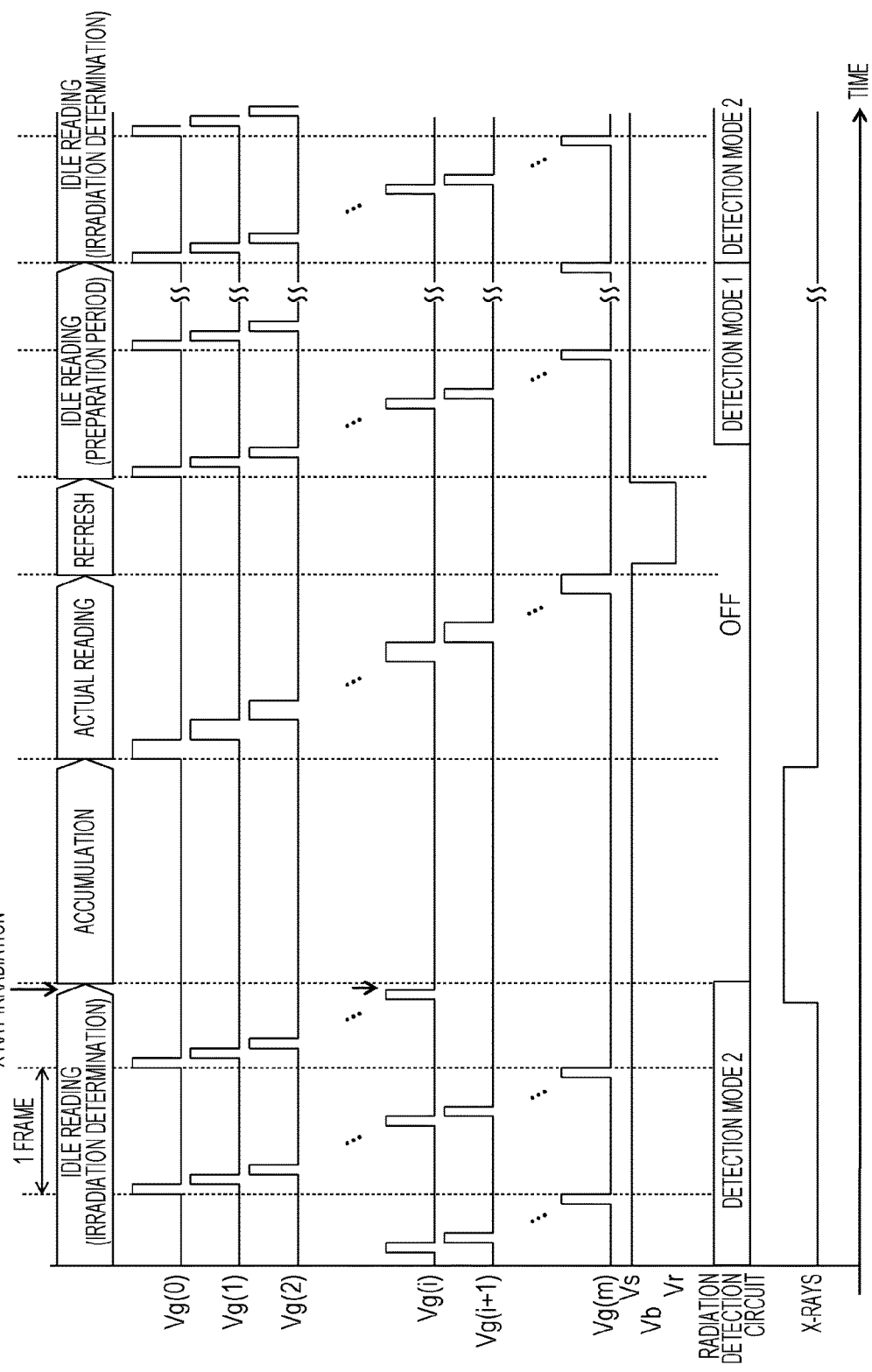
FIG. 16 is a timing chart illustrating how the X-ray imaging apparatus according to the embodiment is driven.

FIG. 16 is a timing chart illustrating driving timings of the X-ray sensor and illustrates the driving timing from the middle of irradiation detection driving (idle reading driving).

Idle reading driving is driving for turning on the switch elements sequentially from the first line (y=0) to the last line (y=m) and is performed to remove electric charges of dark current generated in the photoelectric converter element. Idle reading driving is repeated at regular intervals until irradiation of X-rays is detected. During this period, the bias voltage Vb is maintained to Vs all the time.

In response to irradiation of X-rays, an amount of electric charges read by idle reading increases. At that time, the current flowing through the bias line also increases. The current information on the bias current is input to the X-ray radiation detection circuit, and consequently the start of irradiation of X-rays is detected. At that time, every time idle reading is performed for a line, integration is performed so that the sampled value X[n] is added and the start of irradiation is determined by comparing the integral with a certain threshold.

Upon the start of irradiation of X-rays being determined, the idle reading driving is stopped (the start of irradiation is detected for the i-th line in FIG. 15(*a*)) and the photoelectric converter element starts an electric charge accumulation operation. During accumulation, all the switch elements are kept off. Upon accumulation ending after a certain period has passed, the photoelectric converter elements start actual reading. Actual reading is performed by turning on the switching elements sequentially from the first line (y=0) to the last line (y=m).

After actual reading ends, refreshing is performed thereafter. Refreshing is performed by setting the bias voltage Vb to Vr. Refreshing may be performed collectively on all lines or sequentially. Alternatively, the lines may be grouped into some blocks, and refreshing may be performed on a block-by-block basis. After refreshing ends, idle reading is started again.

Since the current signal used to detect irradiation of X-rays is not obtainable during the accumulation operation, actual reading, and the refreshing operation, it is impossible to detect irradiation of X-rays. Accordingly, the X-ray irradiation detection circuit is turned off. In addition, the current signal is unstable immediately after the mode is switched from the refresh mode to the photoelectric conversion mode. Until the current signal becomes stable, the accuracy of detection of X-ray irradiation decreases and an "erroneous detection", in which it is detected that X-rays are radiated regardless of the fact that X-rays are not radiated, may occur. In such a case, the detection circuit is sometimes turned off for a certain period.

However, when X-rays are mistakenly radiated while the irradiation detection circuit is kept off, the irradiation is not detected, and consequently, a patient who is a subject may be unnecessarily exposed to radiation. In addition to this, the following issues may occur.

In response to irradiation, electric charges are generated in the photoelectric converter element as usual. The generated electric charges are gradually removed by idle reading but electric charges that are not removed accumulate. If the preparation period ends and imaging is performed in this state, the remaining part of the electric charges generated by the erroneous irradiation is added to electric charges generated in the imaging, serving as a cause of decreasing the image quality of the resulting image.

In addition, in the case where the preparation period ends immediately after the erroneous irradiation and detection is started, a large amount of electric charges generated by erroneous irradiation still remains. Thus, lots of electric charges are read by idle reading performed immediately after the detection circuit starts operating, and consequently irradiation may be erroneously detected and an image may be output. At that time, because imaging is not actually performed, the image quality of the obtained image is below a certain level and it is highly likely that the image is not appropriately usable for making a diagnosis. Such an image requires the radiographer to perform, for example, a failed image processing, and can be a cause for increasing the work of the radiographer.

Further, the electric charges generated by the erroneous irradiation cause the photoelectric converter element to be in the state illustrated in part (c) of FIG. 15(*b*), and consequently the image quality significantly decreases as a result of the dynamic range of the image becoming narrower due to a decrease in the sensitivity of pixels to light or a decrease in the saturation level for the incident light. In addition, the sensitivity of detecting irradiation of X-rays also decreases, appropriate irradiation is not detected accurately and the patient may be unnecessarily exposed to radiation repeatedly.

To address such issues and minimizes unnecessary irradiation of patient with radiation, it is necessary to detect that radiation is performed during an inappropriate period and to refresh the photoelectric converter element. To this end, it is desirable to make the preparation period as short as possible and to perform detection of irradiation of X-rays for a period as long as possible. In the embodiment, the photoelectric converter element has a plurality of detection modes and performs detection of irradiation immediately after refresh driving by changing the detection mode in the preparation period and the detection period.

FIG. 16 illustrates the case where the photoelectric converter element has two detection modes. The two detection modes are switched between in synchronization with a timing at which the preparation period is switched to the irradiation determination period. The photoelectric converter element is driven in a detection mode 1 during the preparation period (period that is not the valid imaging period) and in a detection mode 2 during the radiation determination period (the valid imaging period).

The preparation period is a period that follows refreshing and in which the current signal used for detecting irradiation of X-rays and an offset component are unstable. The similar setting may be used immediately after the startup of the X-ray imaging apparatus in addition to immediately after refresh driving. The length of the preparation period may be set to a given value within a range where the image quality and other factors are ensured, and is set to, for example, 10 seconds. The length of the preparation period may be the same immediately after the startup and immediately after refresh driving or may be set separately. Further, for example, by monitoring the state of the current information by using the irradiation detection circuit, the preparation period may be automatically switched in accordance with the state of the current information, such as setting a period up until the current information becomes sufficiently stable as the preparation period. The required degree of stability of the current information may be set in a given manner with consideration of the image quality and the like.

In the embedment, different detection thresholds are used in the detection mode 1 and the detection mode 2. When T1 denotes the threshold in the detection mode 1 and T2 denotes the threshold in the detection mode 2, T1 T2 is satisfied. The detection mode 1 is a mode corresponding to the preparation period in which the current information is unstable, and the threshold is set to high to prevent erroneous detection due to noise or the like.

Figure 17:
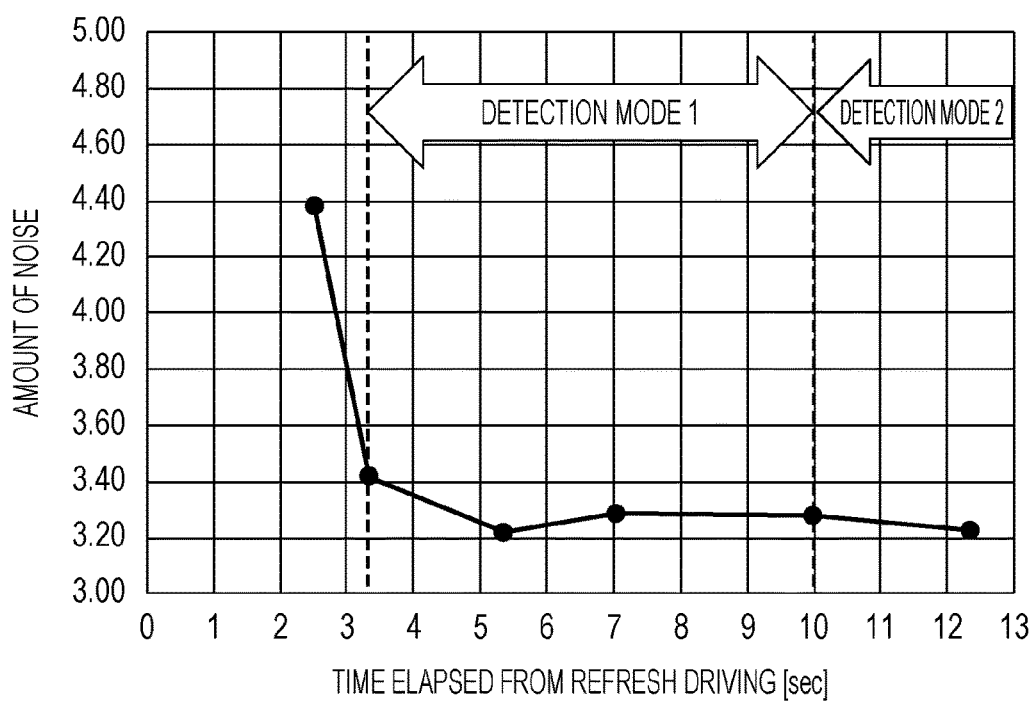
FIG. 17 is a graph illustrating a temporal change in noise in current information in stabilizing driving of the X-ray sensor according to the embodiment.

FIG. 17 is a graph illustrating a temporal change in an amount of noise contained in the current information. The values of the standard deviation ($\sigma$) of noise in the current information at respective time points relative to the timing of refresh driving are plotted. Figure indicates that the amount of noise abruptly decreases immediately after refresh driving and becomes substantially stable after a certain period (5 seconds in the figure). It is assumed here that the detection mode 1 is set for a period from 3 seconds to 10 seconds, during which an abrupt change in noise is settled to some degree. The threshold T1 in the detection mode 1 can be set to an integer multiple of noise ($\sigma$) so that potential erroneous detection due to a change in noise can be suppressed. For example, T1=17, which is five times as large as $\sigma(3.4)$ at 3 seconds, is set. On the other hand, the detection mode 2 is started after the elapse of 10 seconds. T2 may be set to 3.26×5=15.3.

Alternatively, in the case where detection is performed by using a plurality of integrators, it is possible to perform control so that the numbers of integrators operated to be used in detection in the detection mode 1 and the detection mode 2 are different.

In general, when the integration interval of the integrator is small, the capability of handling imaging performed at a high output in a short irradiation period is high, whereas when the integration interval is large, the opposite is true. In addition, when the integration interval is large, a small offset of the current information is accumulated. Thus, erroneous detection is likely to occur when the current information is unstable.

Accordingly, only integrators having small integration intervals may be operated in the detection mode 1 which is set in the preparation period after refreshing, and all the integrators may be operated in the detection mode 2. For example, in the case where the number of integration intervals M is 4, the first integration interval W[1]=8, the second integration interval W[2]=16, the third integration interval W[3]=32, and the fourth integration interval W[4]=64, only integrators for W[1] and W[2] are operated in the detection mode 1. In the detection mode 2, all the integrators for W[1] to W[4] are operated.

In addition to the above-described processing, in another embodiment, the integrators for W[1] to W[4] are gradually operated in accordance with the elapsed period from refresh driving. In this case, the threshold is simultaneously changed in accordance with the change in the current information. Such a configuration makes it possible to stably perform detection immediately after the photoelectric converter element becomes ready.

Upon detection of irradiation of X-rays, an image is accumulated regardless of the detection mode, and upon the end of readout of the image, refresh driving of the element is performed. As a result of refresh driving, the internal state of the detection element is reset, and the detection element can achieve a desired performance in the next imaging. The read image is subjected to image processing and then stored in the image storage unit.

The image captured upon detection in the detection mode 1 during the preparation period may have an image quality that does not reach a desired level because imaging is performed when the offset component is unstable. The use of such an image for making a diagnosis may involve a risk that leads to an incorrect diagnosis or oversight of a lesion, requiring careful handling. Accordingly, the indication illustrated in FIG. 5 is displayed, thereby prompting the user to perform an operation by indicating that the image is highly likely to be a failed image and to handle the image carefully.

Figure 18:
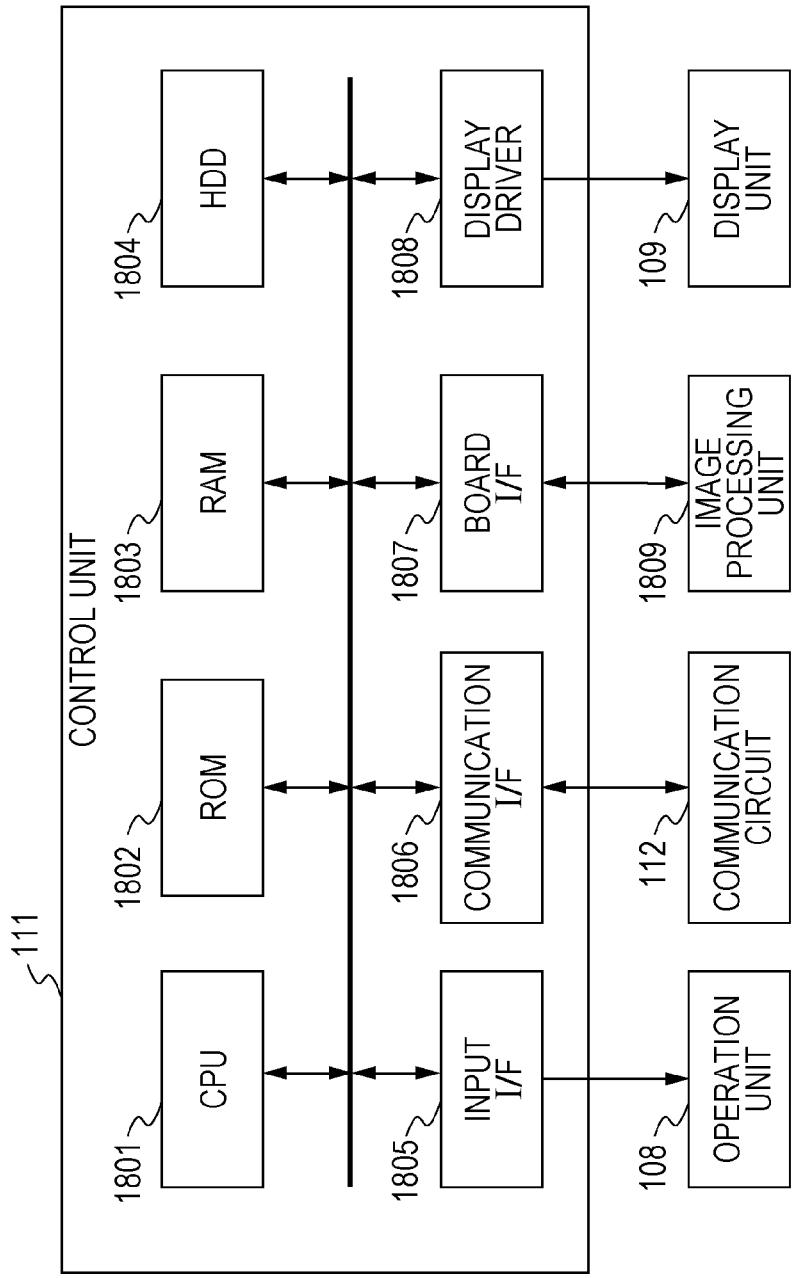
FIG. 18 is a configuration diagram illustrating an example of a hardware configuration of the imaging information processing apparatus according to the embodiment.

Based on FIG. 18, provided is a configuration diagram illustrating an example of a hardware configuration of the imaging information processing apparatus according to the embodiment. The control unit 111 includes a CPU 1801, a ROM 1802, a RAM 1803, an HDD 1804, an input I/F 1805, a communication I/F 1806, a board I/F 1807, and a display driver 1808, which are connected to one another via a bus such as a data bus. The CPU 1801 controls the entire control unit 111 and performs control by executing an instruction program stored in the ROM 1802. Such a program is executed by the CPU 1801 to allow the control unit 111 to exert functions of the imaging control unit 201, the display control unit 202, the input detection unit 203, the information generation unit 204, the storage control unit 205, the specifying unit 206, the failed image setting unit 207, and the image output control unit 208. In addition, such a program is a computer-readable program for implementing the processes illustrated in FIGS. 6 to 9, FIG. 11, and FIG. 13 described below.

The CPU 1801 controls input/output to the display unit 109 via the display driver 1808 and controls input/output to the operation unit 108 via the input I/F 1805. The RAM 1803 allocates a work memory space when the CPU performs control auxiliary storage device that stores various kinds of data, such as X-ray image data. The communication I/F 1806 is a communication interface included in the communication circuit 112 and allows the control unit 111 to send and receive data to and from the X-ray control unit 104, the X-ray detector 106, and the network 113. The board I/F 1807 is included in the image processing unit 1809 and performs, with the GPU, image processing such as gradation processing, noise reduction processing, contrast correction processing, or MTF improving processing, or any combination thereof. Embodiments of the present invention include the above-described program and a non-transitory storage medium, such as a CD, a DVD, or a flash memory, that stores the program thereon.

In the embodiment described above, the example of detecting irradiation of X-rays based on the current flowing through the bias power supply 1006 is presented as the X-ray irradiation detection unit 1062; however, the embodiment is not limited to this example. For example, the reading circuit 1008 may continuously read electric signals from all pixels or a specific pixel and may detect irradiation based on these electric signals. Alternatively, although detection is performed based on the current flowing through the bias power supply 1006, irradiation of X-rays may be detected based on the current flowing through the bias power supply 1006 when the two-dimensional imaging element 1005 is set in the accumulation state.

In the example described above, the X-ray imaging apparatus 106 and the imaging information processing apparatus 107 communicate with each other wirelessly or with a cable; however, the configuration is not limited to this example. The X-ray imaging apparatus 106 and the imaging information processing apparatus 107 may be integrated. In this case, a module corresponding to the X-ray imaging apparatus 106 and a module corresponding to the imaging information processing apparatus 107 perform inter-module communication.

Processes according to other embodiments will be described below.

Figure 19:
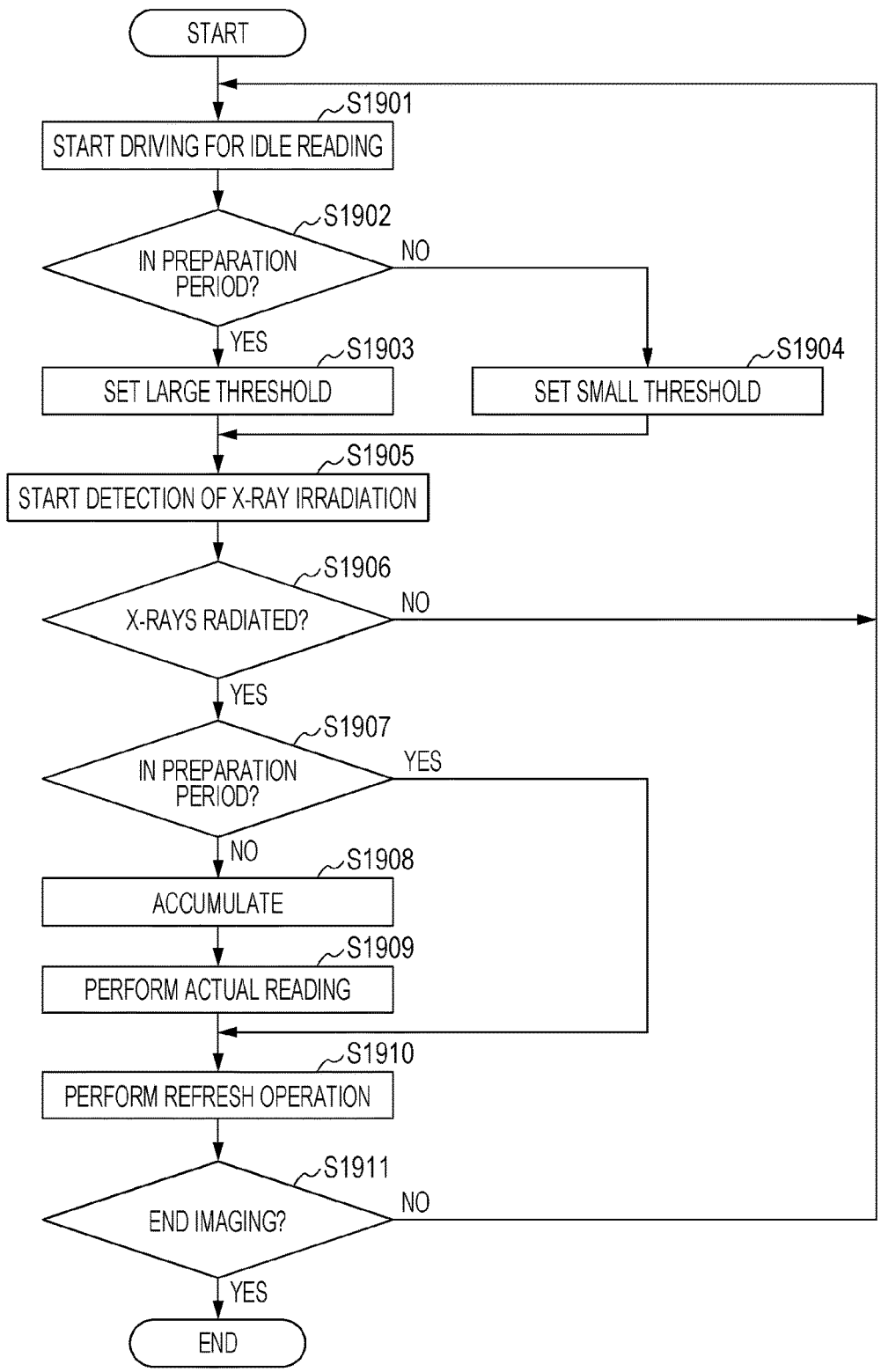
FIG. 19 is a flowchart illustrating a flow of a process according to the embodiment.

FIG. 19 is a flowchart describing an example of a process performed by the X-ray imaging apparatus 106. Upon the X-ray imaging apparatus 106 and X-ray generation unit 102 are started up to start capturing of an X-ray image, the flowchart of FIG. 19 starts. In step S1901, the X-ray imaging apparatus 106 (the driving circuit 1007) starts idle reading driving immediately after the startup. Note that the X-ray imaging apparatus 106 may perform a refresh operation after the startup and then start idle reading driving.

After the start of idle reading driving, the X-ray imaging apparatus 106 (the imaging control unit 1011) determines whether it is the preparation period in step S1902. As a result of the determination, if it is the preparation period, the process proceeds to step S1903, in which the X-ray imaging apparatus 106 (the imaging control unit 1011) sets a threshold for the detection mode 1 (a threshold greater than a threshold for the detection mode 2). Then, the process proceeds to step S1905 described later.

On the other hand, if it is not the preparation period, the process proceeds to step S1904, in which the X-ray imaging apparatus 106 (the imaging control unit 1011) sets the threshold for the detection mode 2 (the threshold smaller than the threshold for the detection mode 1). Then, the process proceeds to step S1905. Note that steps S1902 to S1904 may be performed prior to step S1901.

Figure 14:
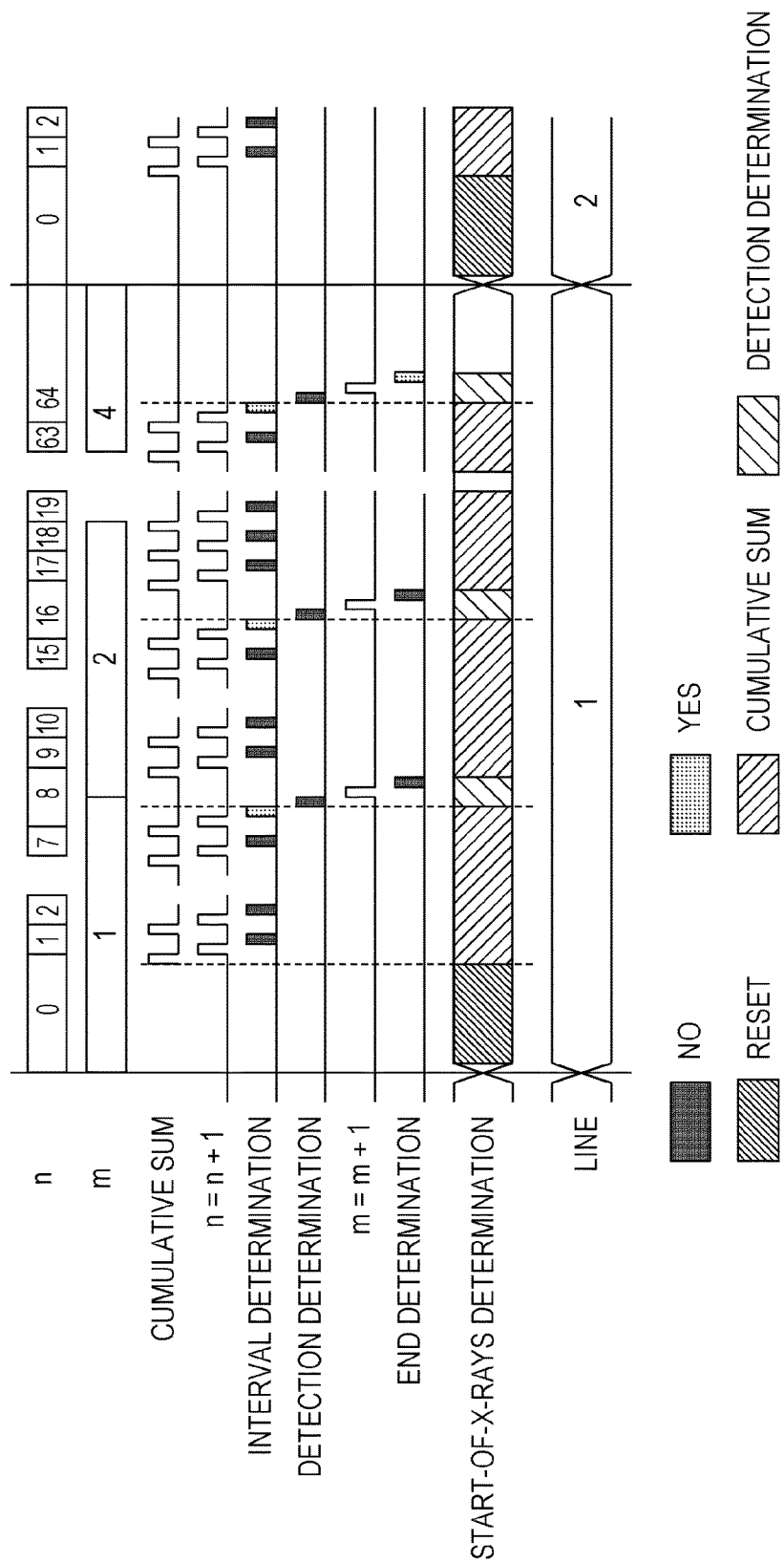
FIG. 14 is a timing chart illustrating an operation performed by the X-ray irradiation detection unit according to the embodiment.

Once the process proceeds to step S1905, the X-ray imaging apparatus 106 (the X-ray irradiation detection unit 1062) starts detection of irradiation of X-rays. After starting detection of irradiation of X-rays, the X-ray imaging apparatus 106 (the X-ray irradiation detection unit 1062) determines in step S1906 whether it is irradiated with X-rays based on a change in current flowing through the bias line, the change being caused by irradiation of X-rays. In this determination, the threshold set in step S1903 or S1904 is used. In addition, the processing of step S1905 and S1906 is performed as described above with reference to FIG. 13 and FIG. 14, for example. As described above, the current information on the bias line may be used in the determination in step S1906 without processing it.

As a result of this determination, if irradiation of X-rays is not detected, idle reading driving is continued. On the other hand, if irradiation of X-rays is detected, the X-ray imaging apparatus 106 (the imaging control unit 1011) determines in step S1907 whether a timing at which irradiation of X-rays has been detected is within the preparation period.

As a result of this determination, if it is determined that the timing at which irradiation of X-rays has been detected is not within the preparation period, the process proceeds to step S1908.

Once the process proceeds to step S1908, the X-ray imaging apparatus 106 (the driving circuit 1007) stops idle reading driving and enters the mode for accumulating electric charges generated in the two-dimensional imaging element 1005 by irradiation of X-rays. Accumulation of electric charges may be performed for a pre-set certain period, or the end of irradiation of X-rays may be detected and a timing at which accumulation of electric charges ends may be controlled based on the detected result. After accumulation of electric charges ends, the X-ray imaging apparatus 106 (the reading circuit 1008) reads electric charges accumulated in the two-dimensional imaging element 1005 (performs actual reading) in step S1909. Image data obtained by actual reading is sent to the imaging information processing apparatus 107.

After actual reading ends, the process proceeds to step S1910, in which the X-ray imaging apparatus 106 (the driving circuit 1007) performs a refresh operation to recover the sensitivity of the photoelectric converter elements S11 to S33. Then, in step S1911, the X-ray imaging apparatus 106 (the imaging control unit 1011) determines whether to end capturing of the X-ray image based on an operation by the radiographer or the like. If capturing of the X-ray image is not ended as a result of this determination, idle reading driving is started again. On the other hand, if capturing of the X-ray image is ended, the process indicated by the flowchart of FIG. 19 ends.

In step S1907, if it is determined that the timing at which irradiation of X-rays has been detected is a timing within the preparation period, the process proceeds to step S1910 without steps S1908 and S1909. That is, the refresh operation is performed immediately without accumulation of electric charges and actual reading. In this way, a decrease in the image quality of the X-ray image or in the X-ray detection sensitivity caused as a result of the influence of X-rays radiated during the preparation period remaining in the next imaging can be effectively prevented. However, as described above, accumulation of electric charges and actual reading may be performed regardless of whether the timing at which irradiation of X-rays has been detected is a timing within the preparation period (that is, processing of step S1907 may be omitted).

By performing processing in a manner as described above, the sensitivity of the X-ray irradiation detection unit 1062 is decreased in a period for which irradiation of X-rays is not recommended. Now, the following situation is considered. Suppose that X-rays are radiated using the same radiation conditions in a period for which irradiation of X-rays is not recommended and in a period for which irradiation of X-rays is recommended. With this setting, a time from when X-rays reach the X-ray imaging apparatus 106 (irradiation of X-rays is started) to when the X-ray irradiation detection unit 1062 actually detects the start of irradiation of X-rays is longer in the case where X-rays are radiated in the period for which irradiation of X-rays is not recommended. Conversely, the period from when X-rays reaches the X-ray imaging apparatus 106 to when the X-ray irradiation detection unit 1062 actually detects the start of irradiation of X-rays is shorter in the case where X-rays are radiated in the period for which irradiation of X-rays is recommended.

As described above, the threshold to be compared with the sum of the current signal that flows from the photoelectric converter element to the bias line in response to irradiation of X-rays is changed depending on the time elapsed from when refreshing of the photoelectric converter element ends (or the X-ray imaging apparatus 106 is started up). Specifically, the threshold in the preparation period (the detection mode 1) in which the time elapsed from when refreshing ends (from the startup) is relatively small is set larger than the threshold in the following irradiation determination period (the detection mode 2). Thus, erroneous detection (such as the start of irradiation of X-rays being detected even when X-rays are not radiated) can be suppressed in the preparation period and it is possible to correctly discriminate between detection of actual X-ray irradiation and other erroneous detection. Accordingly, obtaining X-ray images not usable for making a diagnosis can be suppressed. In the X-ray imaging system capable of performing imaging without electrical connection between the X-ray imaging apparatus 106 and the X-ray generation unit 102, inconveniences caused by irradiation of X-rays in the preparation period of the X-ray imaging apparatus 106 can be suppressed.

In this embodiment, the case of two detection modes, i.e., the detection modes 1 and 2, has been described by way of example; however, the number of detection modes is not limited to two and may be three or more. In such a case, for example, a plurality of thresholds, the number of which is equal to the number of detection modes, may be switched between in accordance with the state of the current signal on the bias line. For example, a configuration may be employed in which the current signal on the bias line is monitored by using the X-ray irradiation detection unit 1062 and the threshold is continuously changed depending on the state of the current signal. By optimizing the threshold used to detect the start of irradiation of X-rays depending on the time in this way, occurrence of X-ray erroneous detection can be suppressed even if X-rays are radiated at an inappropriate timing.

In addition, in this embodiment, the case of comparing the sum of the current signal that flows to the bias line from the photoelectric converter elements S11 to S33 in response to irradiation of X-rays with the threshold has been described by way of example; however, the sum of the current signal that flows to the bias line is not necessarily required to be compared with the threshold as long as a physical quantity that changes in the X-ray detector 110 in response to irradiation of X-rays is compared with a threshold. In addition, it is not necessary to compare the sum of the current signal that flows to the bias line from the photoelectric convertor elements S11 to S33 in response to irradiation of X-rays with the threshold in both the detection mode 1 and the detection mode 2. For example, in the detection mode 2, a peak value of the current signal that flows to the bias line from the photoelectric converter elements S11 to S33 in response to irradiation of X-rays may be compared with the threshold. In the case of this configuration, the threshold for the detection mode 2 is preferably set in accordance with the capability (tube current) of the X-ray generation unit 230. Conversely, in the detection mode 1, the peak value of the current signal that flows to the bias line from the photoelectric converter elements S11 to S33 in response to irradiation of X-rays may be compared with the threshold.

In addition, the relationship of the rows and the columns of the two-dimensional imaging element 1005 may be opposite. That is, reading of pixel signals performed by the reading circuit 1008 on a column-by-column basis may be performed on a row-by-row basis, and driving of pixels performed by the driving circuit 1007 on a row-by-row basis may be performed on a column-by-column basis.

In addition, in the embodiment, the period from when X-rays reach the X-ray imaging apparatus 106 (irradiation of X-rays is started) to when the X-ray irradiation detection unit 1062 actually detects the start of irradiation of X-rays is changed by changing the threshold of the X-ray irradiation detection unit 1062, for example; however, the embodiment is not limited this one. The period from when X-rays reach the X-ray imaging apparatus 106 (irradiation of X-rays is started) to when the X-ray irradiation detection unit 1062 actually detects the start of irradiation of X-rays may be controlled by the circuit configuration of the X-ray irradiation detection unit 1062 or other methods such as adjusting voltage, resistance, or the like.

Second Embodiment

A second embodiment of the present invention will be described next.

In the first embodiment, the case where the number of integrators used in detection of X-rays is fixed has been described by way of example. In contrast, in this embodiment, X-rays are detected by using a plurality of integrators, and the numbers of integrators operated for use in detection are set different in the detection mode 1 and the detection mode 2. As described above, this embodiment and the first embodiment differ in that part of the configuration and processing for detecting X-rays is different. Accordingly, a detailed description of this embodiment for part that is the same as that of the first embodiment is omitted.

In general, when the integration interval of the integrator is small, the capability of handling imaging performed in the case where X-rays are high output and the X-ray irradiation period is short. When the integration interval is large, the opposite is true. In addition, when the integration interval is large, a small offset of the current information is accumulated in the integral. Thus, erroneous detection is likely to occur when the current information is unstable.

Accordingly, only integrators assigned small integration intervals can be operated in the detection mode 1 that is set in the preparation period following the refresh operation and the startup, and all of the integrators can be operated in the detection mode 2. For example, it is assumed that the number of integration intervals M is 4, the width W[1] of the first integration interval is 8, the width W[2] of the second integration interval is 16, the width W[3] of the third integration interval is 32, and the width W[4] of the fourth integration interval is 64. In this case, integrators operated in the detection mode 1 and the detection mode 2 can be set in the following manner. Specifically, in the detection mode 1, only integrators for the first integration interval and the second integration interval are operated. On the other hand, in the detection mode 2, all the integrators for the first to fourth integration intervals are operated.

In addition, in the detection mode 1, the number of integrators operated may be changed depending on the time elapsed from the refresh operation or the startup. For example, when X-rays are detected at a timing after a long time has elapsed from the refresh operation or the startup, the number of integrators operated can be increased. Specifically, for example, in the detection mode 1, integrators for the first integration interval, the second integration interval, the third integration interval, and the fourth integration interval may be sequentially operated in this order in proportion to the elapsed time. For example, from when the elapsed time is zero to when the elapsed time is a first timing, only one integrator for the first integration interval is operated. Thereafter, from the first timing to a second timing, only two integrators for the first integration interval and the second integration interval are operated. Similarly, from the second timing to a third timing, only three integrators for the first to third integration intervals are operated. From the third timing to a fourth timing, four integrators for the first to fourth integration intervals are operated. At that time, the threshold may be changed depending on the elapsed time. For example, the threshold may be made smaller in proportion to the elapsed time.

By optimizing the integrators to be operated in accordance with the period in this manner, it is possible to handle irradiation of X-rays at an inappropriate timing while suppressing occurrence of an erroneous detection.

As described in the embodiment above, a PIN photodiode can be used. In this case, resetting driving can be replaced with output of electric charges by the switching elements T11 to T33 if the imaging element is the one transistor imaging element as illustrated in FIG. 10, and the refresh operation is no longer needed. Accordingly, in one embodiment, resetting driving is the same as idle reading (output driving).

In another embodiment, in resetting driving, the on-period of the switch element is made larger than in idle reading. Idle reading (output driving) is driving synchronized with detection of irradiation of X-rays by the X-ray irradiation detection unit 1062. Thus, idle reading is not necessarily implemented in terms of the function of discharging electric charges accumulated in the photoelectric converter element.

As for detection of X-rays based on current flowing through the bias line Vb, an artifact or an image defect resulting from a time difference between a timing at which irradiation of X-rays is actually started and a timing at which the start of irradiation of X-rays is detected. Such a defect has a line-like or band-like shape extending in the row direction. Such a defect should be corrected in following processing; however, it is desirable that the degree of an image defect in each line is suppressed to simplify the correction processing. From this viewpoint, the on-period of the switch element in the idle reading (output driving) is determined. Accordingly, the on-period is at least set to be shorter than in driving for actual reading.

From the above-described viewpoint, in resetting driving subsequent to detection of irradiation of X-rays in a period (period for which irradiation of X-rays is not recommended, "idle reading (preparation period)" in FIG. 16) that is not a valid imaging period (period of idle reading (radiation determination) in FIG. 16), the driving circuit 1007 controls, for example, the signal Vg(i) illustrated in FIG. 16 to make the on-period of the switch element longer than in idle reading in the irradiation determination period, thereby being able to increase the efficiency of discharging electric charges and stabilize the imaging element earlier. In the example of FIG. 16, in the case of a PIN sensor, idle reading in which the on-period of the switch element is set longer is performed in the refreshing period. The degree of a defect caused in each line of the image due to detection of the start of irradiation of X-rays in such period may become larger; however, because such a period is a period for which the image quality is not stable, the obtained image is highly likely to be an image that cannot be used for making a diagnosis. Thus, the degree of the defect is not so problematic.

According to such an embodiment, the driving circuit 1007 continues idle reading driving without setting the two-dimensional imaging element 1005 in the accumulation state if erroneous radiation is detected.

In the above-described embodiment, the functions of the imaging control apparatus (imaging information processing apparatus) 107 may be implemented as a control system by distributing the functions of the imaging control apparatus (imaging information processing apparatus) 107 to a plurality of apparatuses that can communicate with one another. For example, some functions such as image processing may be implemented in an external server. Such an external server may be installed in an X-ray room where the X-ray imaging system is installed or in the operation room and may be connected via a dedicated LAN or may perform communication over a hospital LAN installed in the hospital. Alternatively, such an external server may be installed at a domestic or foreign data center or the like outside the hospital and may mutually exchange data over secure communication such as VPN.

In the embodiments above, the description has been given of the case of capturing X-ray images; however, imaging using other types of radiation, such as α-rays, β-rays, γ-rays, and other electromagnetic waves are encompassed by the embodiments of the present invention.

The present invention is not limited to the embodiments above, and embodiments obtained by appropriately combining the above-described various embodiments without departing from the spirit and scope of the present invention are also included in embodiments of the present invention. Various alterations and modifications can be made.

For example, following claims are attached in order to clarify the scope for which the patent is claimed.

This application is a national phase application of international application PCT/JP2014/067170, filed on Jun. 27, 2014, which is hereby incorporated by reference herein in its entirety, and this application claims the benefit of Japanese Patent Application No. 2013-137047 filed Jun. 28, 2013 and Japanese Patent Application No. 2013-226013 filed Oct. 30, 2013, which are hereby incorporated by reference herein in their entirety.

The invention claimed is:

1. An information processing apparatus comprising:
a communication circuit configured to communicate with an X-ray imaging apparatus, the X-ray imaging apparatus including a detection unit configured to detect irradiation of radiation by photoelectric conversion and an X-ray sensor configured to obtain an X-ray image in response to the detection by the detection unit; and a control circuit, the control circuit being configured to perform a discriminating process of discriminating between a valid imaging period and an invalid imaging period, and a display control process of causing a display unit to display an icon for accepting an operation input instructing whether to receive the X-ray image in response to the detection unit detecting irradiation of radiation in a period determined to be the invalid imaging period.

2. The information processing apparatus according to claim 1, wherein the communication circuit receives at least one of a signal indicating a driving state of the X-ray sensor and a signal from the X-ray sensor indicating completion of preparation for imaging, and wherein the control circuit discriminates between the valid imaging period and the invalid imaging period in response to the receipt.

3. The information processing apparatus according to claim 1, wherein the communication circuit sends, to the X-ray imaging apparatus, a signal for requesting transmission of the X-ray image, in response to an operation input for instructing to receive the X-ray image on the icon.

4. The information processing apparatus according to claim 1, wherein the communication circuit sends, to the X-ray imaging apparatus, a signal for preventing the X-ray image from being sent, in response to an operation input instructing not to receive the X-ray image on the icon.

5. The information processing apparatus according to claim 1, wherein the display control process causes the display unit to display, on the icon, a first icon for accepting an operation input instructing to receive the X-ray image, a second icon for accepting an operation input instructing to receive the X-ray image and set the X-ray image as a failed image, and a third icon for accepting an operation input instructing not to receive the X-ray image.

6. The information processing apparatus according to claim 5, wherein the communication circuit receives the X-ray image in response to an operation input for the third icon, and wherein the information processing apparatus further comprises: a storage unit configured to store the X-ray image in association with information indicating that the X-ray image is a failed image, in response to receipt of the X-ray image.

7. An X-ray imaging system comprising: the information processing apparatus according to claim 1.

8. The X-ray imaging system according to claim 7, further comprising:

an X-ray generation unit; and a display unit.

9. A radiography apparatus, comprising:

a detection circuit configured to detect that irradiation of radiation is started;

an X-ray sensor including a plurality of photoelectric converter elements and configured to obtain an X-ray image in response to detection by the detection circuit; and a driving circuit configured to drive the X-ray sensor;

wherein the detection circuit changes a condition for detecting the start of irradiation of radiation such that the start of irradiation of radiation is less likely to be detected in a case where the start of irradiation of radiation is detected on the basis of electric charges generated by the photoelectric converter elements in a first period than in a case where the start of irradiation of radiation is detected on the basis of electric charges generated by the photoelectric converter elements in a second period.

10. The radiography apparatus according to claim 9, wherein the detection circuit:

detects the start of irradiation of radiation by comparing a physical quantity generated by detection of radiation with a threshold; and changes the threshold in accordance with at least one of an elapsed time from when a resetting operation for outputting electric charges accumulated in the photoelectric converter elements ends and an elapsed time from when the radiography apparatus is started up.

11. The radiography apparatus according to claim 10, wherein the detection circuit detects the start of irradiation of radiation by comparing a sum of a physical quantity generated by detection of radiation with the threshold.

12. The radiography apparatus according to claim 11, wherein the detection circuit detects the start of irradiation of radiation by comparing, for each of a plurality of intervals for measuring the physical quantity used in calculation of the sum, the sum of the physical quantity generated by detection of radiation with the threshold.

13. The radiography apparatus according to claim 12, wherein the detection circuit changes, for each of the plurality of intervals, the threshold in accordance with an amount of noise in the physical quantity.

14. The radiography apparatus according to claim 12, wherein the detection circuit changes a length of the intervals between a case of detecting the start of irradiation of radiation in the first period and a case of detecting the start of irradiation of radiation in the second period.

15. The radiography apparatus according to claim 12, wherein the detection circuit changes a length of the intervals in the first period in accordance with an elapsed time from the start of the first period.

16. The radiography apparatus according to claim 9, wherein the detection circuit:

detects the start of irradiation of radiation by comparing a physical quantity generated by detection of radiation with a threshold; and changes the threshold before and after elapse of at least one of a period from when a resetting operation for outputting electric charges accumulated in the photoelectric converter elements ends to when operation of the radiography apparatus stabilizes and a period from when the radiography apparatus is started up to when operation of the radiography apparatus stabilizes.

17. The radiography apparatus according to claim 9, wherein the first period is a period for which irradiation of radiation is not recommended, and the second period is a period for which irradiation of radiation is recommended.

18. The radiography apparatus according to claim 9, wherein the first period is a period in which the radiography apparatus has not finished preparation for radiography imaging, and the second period is a period in which the radiography apparatus has finished preparation for radiography imaging.

19. An information processing apparatus comprising:

a communication circuit configured to communicate with an X-ray imaging apparatus, the X-ray imaging apparatus including a detection unit configured to detect irradiation of radiation by photoelectric conversion and an X-ray sensor configured to obtain an X-ray image in response to the detection by the detection unit; and a control circuit, the control circuit being configured to perform a discriminating process of discriminating between a valid imaging period and an invalid imaging period, and a display control process of causing a display unit to display an icon for checking that the X-ray image is transferred from the X-ray imaging apparatus in response to the detection unit detecting irradiation of radiation in a period determined to be the invalid imaging period.

20. The information processing apparatus according to claim 19, wherein the icon is a button for transferring the X-ray image stored in the X-ray imaging apparatus.

21. The information processing apparatus according to claim 19, wherein the communication circuit receives at least one of a signal indicating a driving state of the X-ray sensor and a signal from the X-ray sensor indicating completion of preparation for imaging, and wherein the control circuit discriminates between the valid imaging period and the invalid imaging period in response to the receipt.

22. The information processing apparatus according to claim 19, wherein the communication circuit sends, to the X-ray imaging apparatus, a signal for requesting transmission of the X-ray image, in response to an operation input for instructing to receive the X-ray image on the icon.

23. The information processing apparatus according to claim 19, wherein the communication circuit sends, to the X-ray imaging apparatus, a signal for preventing the X-ray image from being sent, in response to an operation input instructing not to receive the X-ray image on the icon.

24. An information processing method comprising:

communicating with an X-ray imaging apparatus, the X-ray imaging apparatus including a detection unit configured to detect irradiation of radiation by photoelectric conversion and an X-ray sensor configured to obtain an X-ray image in response to the detection by the detection unit;

discriminating between a valid imaging period and an invalid imaging period; and causing a display unit to display an icon for accepting an operation input instructing whether to receive the X-ray image in response to the detection unit detecting irradiation of radiation in a period determined to be the invalid imaging period.

25. An information processing method comprising:

detecting that irradiation of radiation is started;

obtaining, via an X-ray sensor including a plurality of photoelectric converter elements, an X-ray image in response to a detection in the detecting step; and driving the X-ray sensor, wherein the detecting step changes a condition for detecting the start of irradiation of radiation such that the start of irradiation of radiation is less likely to be detected in a case where the start of irradiation of radiation is detected on a basis of electric charges generated by the photoelectric converter elements in a first period than in a case where the start of irradiation of radiation is detected on a basis of electric charges generated by the photoelectric converter elements in a second period.

26. An information processing method comprising:

communicating with an X-ray imaging apparatus, the X-ray imaging apparatus including a detection unit configured to detect irradiation of radiation by photoelectric conversion and an X-ray sensor configured to obtain an X-ray image in response to the detection by the detection unit;

discriminating between a valid imaging period and an invalid imaging period, and causing a display unit to display an icon for checking that the X-ray image is transferred from the X-ray imaging apparatus in response to the detection unit detecting irradiation of radiation in a period determined to be the invalid imaging period.

27. An information processing apparatus comprising:

a communication circuit configured to communicate with an X-ray imaging apparatus, the X-ray imaging apparatus including a detection unit configured to detect irradiation of radiation by photoelectric conversion and an X-ray sensor configured to obtain an X-ray image in response to the detection by the detection unit; and a control circuit, the control circuit being configured to perform a determining process of determining whether a period is a valid imaging period or an invalid imaging period, and a display control process of causing a display unit to display an icon to indicate that the X-ray image is transferred from the X-ray imaging apparatus in response to the detection unit detecting irradiation of radiation in the period determined to be the invalid imaging period.

28. The information processing apparatus according to claim 27, wherein the icon is a button for transferring the X-ray image stored in the X-ray imaging apparatus.

29. The information processing apparatus according to claim 27, wherein the communication circuit receives at least one of a signal indicating a driving state of the X-ray sensor and a signal from the X-ray sensor indicating completion of preparation for imaging, and wherein the control circuit determines whether the period is the valid imaging period or the invalid imaging period in response to the receipt.

30. The information processing apparatus according to claim 27, wherein the communication circuit sends, to the X-ray imaging apparatus, a signal for requesting transmission of the X-ray image, in response to an operation input for instructing to receive the X-ray image on the icon.

31. The information processing apparatus according to claim 27, wherein the communication circuit sends, to the X-ray imaging apparatus, a signal for preventing the X-ray image from being sent, in response to an operation input instructing not to receive the X-ray image on the icon.

32. An information processing method comprising:

communicating with an X-ray imaging apparatus, the X-ray imaging apparatus including a detection unit configured to detect irradiation of radiation by photoelectric conversion and an X-ray sensor configured to obtain an X-ray image in response to the detection by the detection unit;

determining whether a period is a valid imaging period or an invalid imaging period, and causing a display unit to display an icon to indicate that the X-ray image is transferred from the X-ray imaging apparatus in response to the detection unit detecting irradiation of radiation in the period determined to be the invalid imaging period.

* * * * *